United States Patent
Scheucher

(10) Patent No.: US 9,335,232 B2
(45) Date of Patent: *May 10, 2016

(54) NETWORK MANAGEABLE ADVANCED GAS SENSOR APPARATUS AND METHOD

(71) Applicant: Solon Manufacturing Company, Chardon, OH (US)

(72) Inventor: Karl Frederick Scheucher, Waite Hill, OH (US)

(73) Assignee: Solon Manufacturing Company, Chardon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/419,625

(22) PCT Filed: Aug. 3, 2013

(86) PCT No.: PCT/US2013/053528
§ 371 (c)(1),
(2) Date: Feb. 4, 2015

(87) PCT Pub. No.: WO2014/025652
PCT Pub. Date: Feb. 13, 2014

(65) Prior Publication Data
US 2015/0204753 A1 Jul. 23, 2015

Related U.S. Application Data

(63) Continuation of application No. 13/568,108, filed on Aug. 6, 2012, now Pat. No. 9,212,966.

(60) Provisional application No. 61/699,835, filed on Sep. 11, 2012, provisional application No. 61/515,834, filed on Aug. 5, 2011, provisional application No. 61/542,261, filed on Oct. 2, 2011.

(51) Int. Cl.
*G01M 3/26* (2006.01)
*G01N 9/26* (2006.01)
(Continued)

(52) U.S. Cl.
CPC ............ *G01M 3/26* (2013.01); *G01M 3/002* (2013.01); *G01N 9/266* (2013.01); *G05B 15/02* (2013.01)

(58) Field of Classification Search
CPC .................. G01M 3/26; G01N 9/266
See application file for complete search history.

(56) References Cited

U.S. PATENT DOCUMENTS 3,046,369 A * 7/1962 Hicks ............... 200/83 C
3,431,785 A * 3/1969 Love ............... 73/434
(Continued)

OTHER PUBLICATIONS

United States Environmental Protection Agency, "Inventory of U.S Greenhouse Gas Emissions and Sinks: 1990-2008", Washington, DC, Apr. 15, 2010, Available at http://www.epa.gov/climatechange/emissions/downloads10/US-GHG-Inventory-201 O_Report.pdf.
(Continued)

*Primary Examiner* — Lisa Caputo
*Assistant Examiner* — Punam Roy
(74) *Attorney, Agent, or Firm* — Baker & Hostetler LLP

(57) ABSTRACT

Mechanical, electronic, algorithmic, and computer network facets are combined to create a highly integrated advanced gas sensor system. The sensor system, utilized with gas insulated high voltage switchgear products, deployed by electric utility end users in replacement and expansion cycles, function to detect and mitigate atmospheric pollution caused by leaking $SF_6$. As its associated gas insulated tank is charged with 10 to 350 lbs. of $SF_6$, each gas sensor monitors its local cache of gas, accurately sensing and computing fractional percentage losses (emissions) and gains (maintenance replacement) in $SF_6$ mass, storing data in onboard data logs, and communicating data when triggered by detection events or in response to remote requests over a hierarchical communications network, a process that continues without labor until a fractional leak is automatically detected and reported creating the opportunity for early leak mitigation.

12 Claims, 23 Drawing Sheets

(51) Int. Cl.
*G01M 3/00* (2006.01)
*G05B 15/02* (2006.01)

(56) References Cited

U.S. PATENT DOCUMENTS

| | | | | | |
|---|---|---|---|---|---|
| 3,576,412 | A | * | 4/1971 | Jullien-Davin | 200/83 R |
| 3,749,865 | A | * | 7/1973 | Kalt et al. | 200/83 R |
| 3,946,175 | A | * | 3/1976 | Sitabkhan | 200/83 L |
| 4,364,271 | A | * | 12/1982 | Froome | 73/866.1 |
| 6,125,692 | A | * | 10/2000 | Marmonier | 73/40 |
| 7,149,374 | B2 | * | 12/2006 | Lagakos et al. | 385/12 |
| 7,249,517 | B2 | * | 7/2007 | Heuer et al. | 73/722 |
| 7,937,985 | B2 | * | 5/2011 | Chambon | 73/1.68 |
| 2012/0318044 | A1 | * | 12/2012 | Halbheer | 73/30.02 |
| 2013/0031958 | A1 | * | 2/2013 | Scheucher | 73/31.05 |

OTHER PUBLICATIONS

Debra Knopman, Katie Smythe, "2004-2006 SF6 Data Summary", PM-2327-NEMA, Jun. 2007, Prepared for the National Electrical Manufacturers Association, Available at http://www.epa.gov/electricpower-sf6/documents/04-06_data_summary.pdf.

United States Environmental Protection Agency, "SF6 Emission Reduction Partnership for Electric Power Systems—2007 Annual Report", Washington, DC, Dec. 2008, Available at http://www.epa.gov/electricpower-sf6/documents/sf6_2007_ann_report.pdf.

Jos Olivier, Joos! Bakker, Jan Willem Wouda, Rainer Bitsch, and Manfred Maiss, "Global Emission Sources of Greenhouse Gas Emissions from Industrial Processes: SF6", IPCC Task Force on National Greenhouse Gas Inventories, Jan. 2003, Available at <http://www.ipcc-nggip.iges.or.jp/public/gp/bgp/3_9_Global_Sources_Industrial_Processes_SF6.pdf.

L. G. Christophorou, J. K. Olthoff, and D. S. Green, "Gases for Electrical Insulation and Arc Interruption: Possible Present and Future Alternatives to Pure SF6", NIST Technical Note 1425, Nov. 1997, Available at <http://www.epa.gov/electricpower-sf6/documents/new_report_final.pdf United States Environmental Protection Agency, "Electric Transmission and Distribution Equipment Use—Final Rule: Mandatory Reporting of Greenhouse Gases (40 CFR 98, Subpart DD)", Nov. 2010, Available at <http://www.epa.gov/climatechange/em issions/downloads 1O/Subpart-DD_infosheet.pdf.

Alfieri, M. 2002. "Partner Case Study: Con Edison", Presented on behalf of Con Edison at the International Conference on SF6 and the Environment: Emission Reduction Strategies. San Diego, CA, Nov. 21-22, 2002. Available at <http://www.epa.gov/highgwp1/sf6/proceedings/agenda.html.

Robert Madding and Robert Benson, "Detecting SF6 Insulating Gas Leaks with an IR Imaging Camera", Electricity Today, pp. 12-15, Nov./Dec. 2007, Available at <http://www.electricity-today.com/et/issue0907/ir_camera.pdf.

Jan-Martin Rhiemenier, Sina Wartmann, Marcello Pagnotta, Natalia Makowska, and Xingyu Li, "Update on global SF6 Emissions trends from electrical equipment—Edition 1.1". Ecofys Germany GmbH, Jul. 2010, Available at <http://www.ecofys.com/com/pub lications/brochures_newsletters/documents/ES I-SF6_Finalreport_edition11_100701_vO1.pdf.

U.S. Department of Energy, "U.S. Energy Information Administration Eletric Power Annual 2009", Washington, DC, Nov. 2010, Available at <http://www.eia.gov/cneaf/electricity/epa/epa_sum.html>.

WIKA Alexander Wiegand GmbH & Co. KG, "Gas Density Monitor (GDM) with Integrated Gas Density Transmitter, Model 233.52.100 TI"Klingenberg, Germany, May 2009, Available at <http://en-co.wika.de/upload/DS_SP6005_GB_7922.PDF.

J. Blackman, M. Averyt, and Z. Taylor, "SF6 Leak Rates from High Voltage Circuit Breakers—U.S. EPA Investigates Potential Greenhouse Gas Emissions Source", presented at the International Conference on SF6 and the Environment: Electric Power Systems—Partnership Update, Nov. 28, 2006, Available at <http://www.epa.gov/electricpower-sf6/documents/leakrates_circuitbreakers.pdf.

General Electric Company, "72.5kV Circuit Breakers Data Sheet", Nov. 10, 1999, Available at <http://www.geindustrial.com/publibrary/checkout/72.5DAT?TNR=Data%20Sheetsl72.5DATIPDF.

General Electric Company, "121kV Circuit Breakers Data Sheet", Mar. 1, 2002, Available at <http://www.geindustrial.com/publibrary/checkout/121 DATA?TNR=Data%20Sheetsl 121DATAIPDF.

General Electric Company, "145kV Circuit Breakers Data Sheet", Nov. 10, 1999, Available at <http://www.geindustrial.com/publibrary/checkout/Data%20Sheetsl 145DATAI PDF.

General Electric Company, "169kV Circuit Breakers Data Sheet", Nov. 10, 1999, Available at <http://www.geindustrial.com/publibrary/checkout/Data%20Sheetsl 169DATAI PDF.

General Electric Company, "242kV Circuit Breakers Data Sheet", Nov. 10, 1999, Available at <http://www.geindustrial.com/publibrary/checkout/Data 0/o20Sheetsl242DA TAI PDF.

General Electric Company, "362kV Circuit Breakers Data Sheet", Nov. 10, 1999, Available at <http://www.geindustrial.com/publibrary/checkout/Data%20Sheetsl362DA TA51PDF.

General Electric Company, "550kV Circuit Breakers Data Sheet", Nov. 10, 1999, Available at <http://www.geindustrial.com/publibrary/checkout/Data%20Sheetsl550DA TA41PDF.

Giancarlo Scalabrin, Luigi Bettio, Paolo Marchi, and Paolo Stringari, "A Fundamental Equation of State for Sulfur Hexafluoride (SF6) in Extended Equation of State Format", JPCRD 36(2) pp. 617-662, 2007, Available at <http://energyfromthorium.com/forum/download/file.php?id=44&sid=275692ae3353e590221e1226f0501ac1.

Maryland Department of the Environment, "Maryland C02 Budget Trading Program, COMAR 26.09.03", Baltimore, MD, Aug. 2009, Available at <http://www.mde.state.md.us/programs/Air/RGG1/Documents/www.mde.state.md.us/ assets/document/air/RGGI/04_SF6_0ffset_FINAL.pdf.

California Environmental Protection Agency, Air Resources Board, "Proposed Regulation Order: Regulation for Reducing Sulfur Hexafluoride Emissions from Gas Insulated Switchgear", Sacramento, CA, Jan. 7, 2010, Available at <http://www.arb.ca.gov/regacl/2010/sf6elec/appa.pdf.

United Nations Framework Convention on Climate Change, "SF6 Emission Reductions in Electrical Grids", Bonn, Germany, Sep. 29, 2006, Available at <http://cdm.unfccc.int!filestorage/CDMWF_AM_5WABPI8CK9HOSTV8E9CKDPFZM7UKQU/EB26_repan02_AM0035_NM0135.pdf?t=ekZ8MTI5MTM5NDM5NS45NA==i3FfpdD3nIBJADrv6dXLw5eW37cE=.

United States Department of the Interior Bureau of Reclamation, "Management and Safe Handling Procedures for Sulfur Hexaflouride (SF6) Gas", Mar. 2004, Available at <http://www.usbr.gov/power/data/fisl/fist5_9/fist5_9.pdf.

* cited by examiner

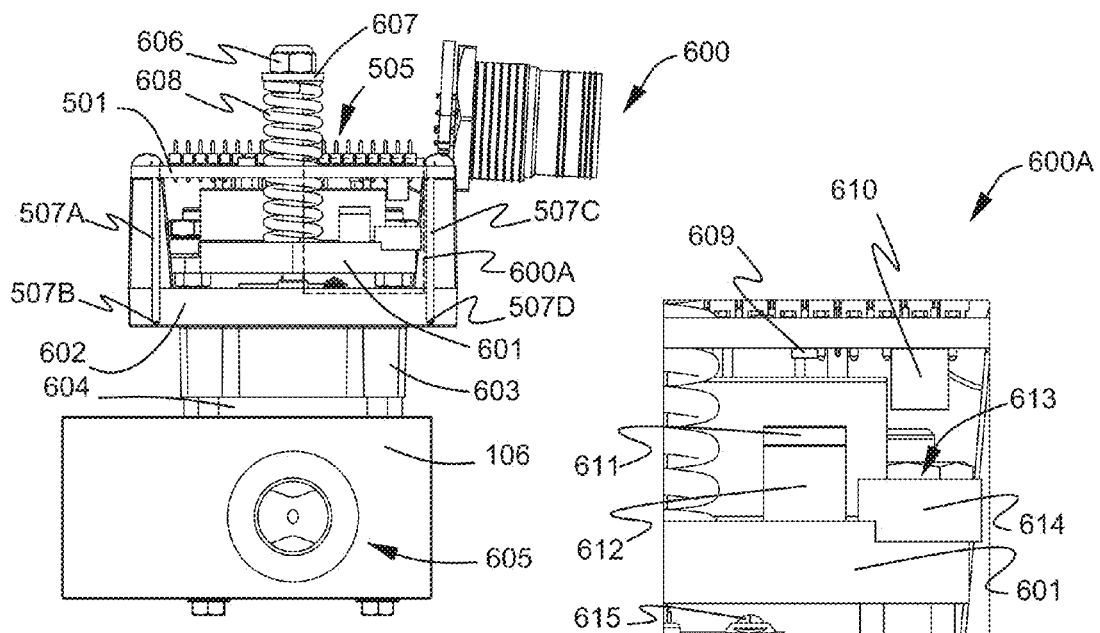
FIG. 6
FIG. 6A
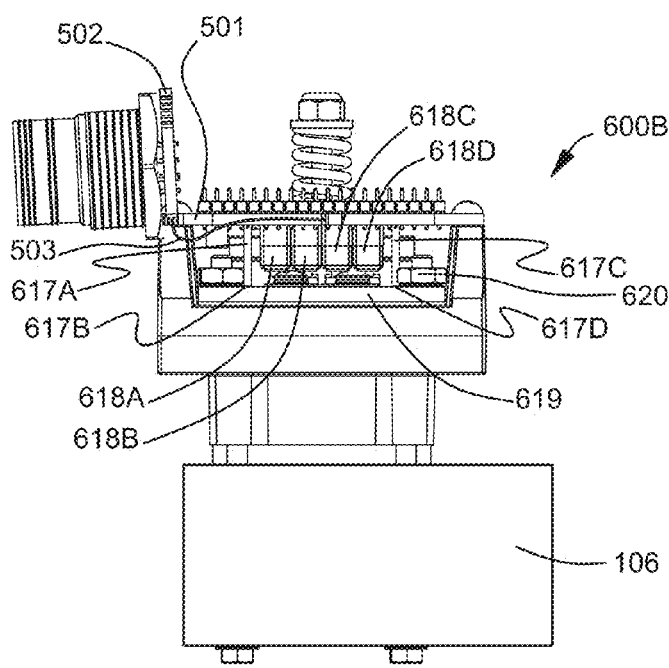
FIG. 6B

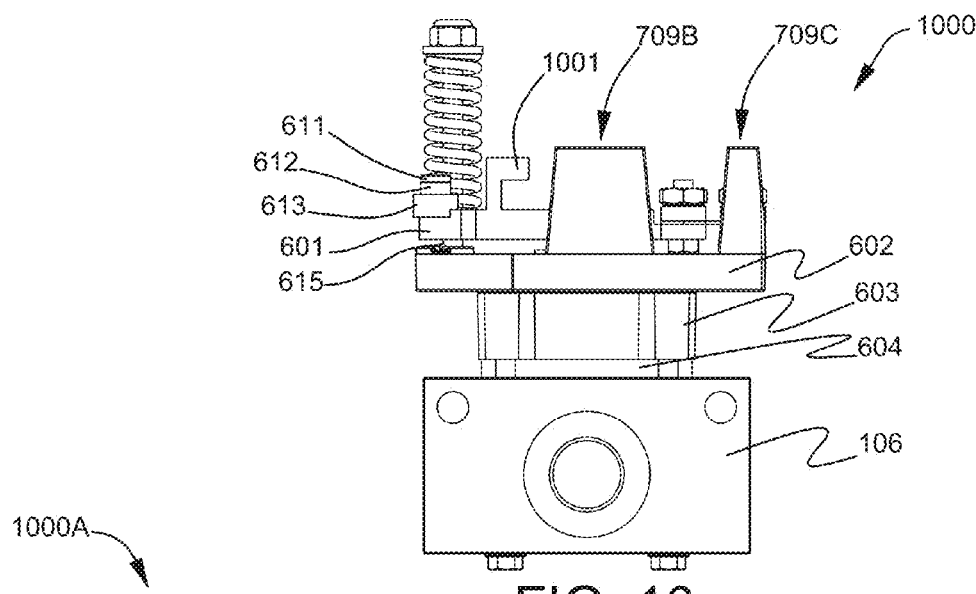
FIG. 10
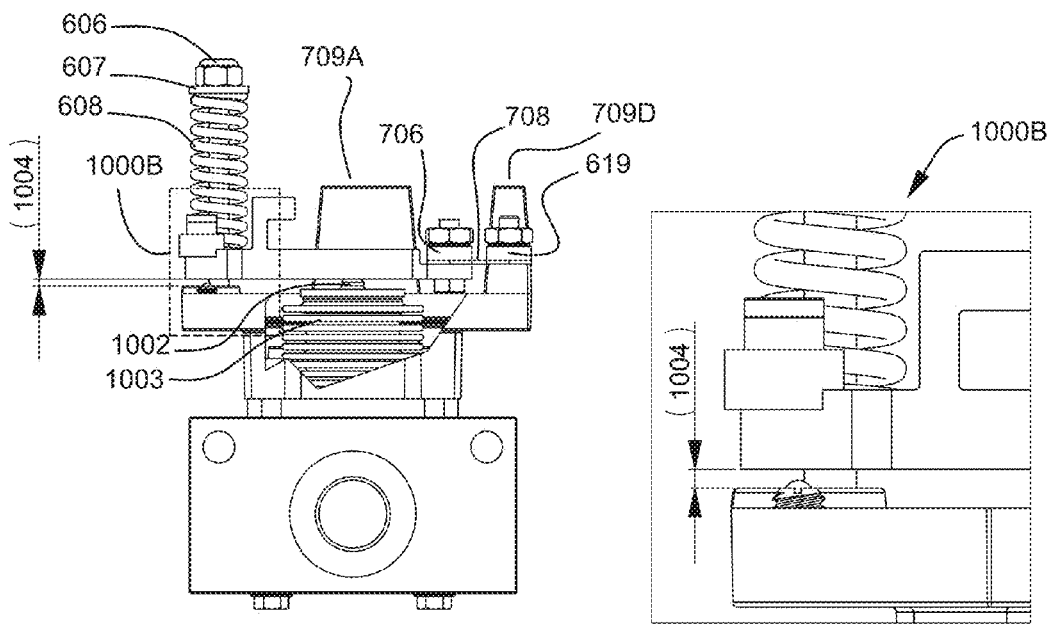
FIG. 10A
FIG. 10B

|  Time | Temp (C) | Pressure (psig) | SF6 (kg) | Alarm State |
|---|---|---|---|---|
| 7/1/12 20:23 | 34.65 | 85.66 | 37.09 | OPERATE |
| 7/1/12 22:47 | 35.92 | 86.05 | 37.08 | OPERATE |
| 7/2/12 01:11 | 37.77 | 86.62 | 37.07 | OPERATE |
| 7/2/12 03:35 | 38.59 | 86.86 | 37.06 | OPERATE |
| 7/2/12 05:59 | 37.65 | 86.53 | 37.05 | OPERATE |
| 7/2/12 08:23 | 40.62 | 87.47 | 37.04 | OPERATE |
| 7/2/12 10:47 | 35.51 | 85.78 | 37.03 | OPERATE |
| 7/2/12 13:11 | 35.03 | 85.59 | 37.02 | OPERATE |
| 7/2/12 15:35 | 36.50 | 86.04 | 37.01 | OPERATE |
| 7/2/12 17:59 | 35.19 | 85.59 | 37.00 | OPERATE |
| 7/2/12 20:23 | 40.55 | 87.31 | 36.99 | OPERATE |
| 7/2/12 22:47 | 34.33 | 85.26 | 36.98 | OPERATE |

FIG. 26

NETWORK MANAGEABLE ADVANCED GAS SENSOR APPARATUS AND METHOD

This application claims priority to: U.S. patent application Ser. No. 13/568,108 filed Aug. 6, 2012 and to U.S. Patent Application No. 61/699,835 filed Sep. 11, 2012.

This application incorporates copending U.S. patent application Ser. No. 13/568,108 filed Aug. 6, 2012 by reference hereto in its entirety. This application incorporates U.S. Patent Application No. 61/699,835 filed Sep. 11, 2012 by reference hereto in its entirety.

This application incorporates U.S. Provisional patent application Ser. No. 61/515,834 filed Aug. 5, 2011 by reference hereto in its entirety. This application incorporates U.S. Provisional patent application Ser. No. 61/542,261 filed Oct. 2, 2011 by reference hereto in its entirety.

FIELD OF THE INVENTION

The field of invention is the field of intelligent gas sensors with the capability to measure the pressure and temperature of one or more target gas substances contained in a known volume and to compute the mass of gas so contained as it varies in time due to additions or losses. The invention is also in the field of intelligent networked sensor nodes that exchange sensor information and sensor configuration and control information over communication networks. The field of invention also includes sensors that measure time-varying environmental conditions such as ambient temperature, atmospheric pressure, ambient light conditions, ambient sound levels, as well as various electrical conditions of equipment adjacent systems including AC and DC voltages and currents. The invention also comprises the field of dielectric gas sensors and gas leakage sensors.

BACKGROUND OF THE INVENTION

There is a clear need for a low cost, network manageable, advanced gas sensor for sulfur hexafluoride gas ($SF_6$) used in high voltage electric switchgear. $SF_6$ plays a crucial arc-suppression role in this equipment. An expensive commodity and a potent greenhouse gas (GWP 23,900 times that of CO2), $SF_6$ lost through leakage is a costly problem justifying an effective monitoring system. The instant invention appreciates the application requirements and the sensor and communications network technologies required to meet them. The invention further supports security aspects that are paramount and tolerates the outdoor substation application environment which is challenging.

Worldwide, of 7 million kg of $SF_6$ produced annually, most (~75% or 5.5 metric tones per annum) is used for electric power equipment. Consequences for the environment and cost implications for electrical energy producers and users are clearly conveyed. Lower-impact, lower-cost alternatives to $SF_6$, though sought, are not found. Techniques for estimating emissions have been based predominately upon indirect, mass-balance accounting methods that are costly and error-prone. Trials using expensive equipment (e.g. IR camera) combined with substantial labor have nonetheless shown that environmental impacts and gas expense arising from leakage are significant and can be reduced.

Presently, $SF_6$ contributes 3% $CO_2$-equivalent emissions. As global electric usage ($3\times10^6$ Wh/capita) ascends to U.S. levels ($1.3\times10^7$ Wh/capita), global generation increases 5-fold. While $CO_2$ emission per kWh generated must surely decrease, $SF_6$ emissions will scale with distribution. Switchgear equipment manufacturers and utilities need a low cost, network manageable, advanced gas sensor to achieve reductions in $SF_6$ emissions per kWh.

All electric producers and users benefit. The instant invention targets economical, distributed sensor technology that can be applied worldwide to achieve a 100-fold reduction in emissions rate—a tremendous opportunity for the environment and economies worldwide.

SUMMARY OF THE INVENTION

Although this patent application emphasizes use of the invention for sensing $SF_6$ in electric breaker applications, it is an important goal of the invention to be readily adaptable to many different gases and gas mixtures used in a broad range of processes.

This invention combines the mechanical, electronic, algorithmic, and network facets needed to create a technology platform for highly integrated gas sensors. These sensors are of great value to electric utility companies and therefore to the manufacturers of equipment used by the utilities. A sensor will be usefully integrated into each gas insulated tank of each breaker and switch unit manufactured (tens of thousands of sensors). These sensors integrated into high voltage switchgear products, deployed by electric utility end users in replacement and expansion cycles, function to detect and mitigate atmospheric pollution caused by leaking $SF_6$. As its associated gas insulated tank is charged with 10 to 350 lbs. of $SF_6$, each gas sensor monitors its local cache of gas, accurately sensing and computing fractional percentage losses (emissions) and gains (maintenance replacement) in $SF_6$ mass, storing data in onboard data logs, and communicating data when triggered by detection events or in response to remote requests over a hierarchical communications network, a process that continues without labor until a fractional leak is automatically detected and reported creating the opportunity for early leak mitigation. Sensors also detect and log repair events including the addition of gas made to replace losses, thus closing the overall monitoring and mitigation loop.

Although a variety of devices and systems for monitoring and measuring aspects of $SF_6$ gas in laboratory and field settings are currently described in the research and trade literature, none represent a fully integrated, economical, network interface-able component for automatically monitoring $SF_6$ gas trends in real-time on a tank-by-tank globally distributed basis. Approaches based upon IR imaging such as EPRI and FLIR devices are expensive in both equipment and labor and therefore find use monitoring for gas leaks only on a spot versus continuous basis.

High voltage breakers and gas insulated switchgear (GIS) require their $SF_6$ content to be carefully monitored and controlled. Arc-suppression safety becomes an issue when gas supply is insufficient. Overpressure is problematic with excess gas levels. Determining that gas levels are in the desired range is generally achieved by gas density estimates which in turn are generally derived from gas pressure measurements appropriately compensated for temperature variations. The well known ideal gas law provides a simple model which conveys the concept:

$$pV = nRT \therefore \frac{n}{V} = \frac{p}{RT} \tag{1}$$

Where P is gas pressure in the system, V is the volume of gas which is fixed by the equipment's rigid tank, R is a constant, T is temperature, and n is the mass quantity of gas. With V and R constant, measuring P and T determines n/V, the gas density.

Two types of products have been developed which address the gas content control task. One type, which may generally be referred to as a gas density "monitor", detects gas density by comparing relatively few thresholds such as: a) high limit, b) nominal limit, c) low limit, and d) low lockout limit. This allows the user to resolve gas density into one of five broad bins: 1) above a, 2) between a and b, 3) between b and c, 4) between c and d, and 5) below d. As illustrated in table 1, while this information is sufficient to enforce the above mentioned safety functions, it falls short of the resolution needed for meaningful emissions mitigation. Manufacturers producing gas density monitor-type products include Solon Manufacturing, Wika, and Comde. In general, these products, unlike IR cameras, are relatively low cost (under $1 k USD), of a simple and robust design, well accepted in the marketplace, and therefore in wide use.

A second type of product for gas control applications may generally be referred to as a gas density "transmitter". This variant measures gas parameters including pressure and temperature to higher resolution, incorporates electronics to derive a temperature compensated density from those measurements, and transmits a density proportional electrical output such as the standard 4-20 mA current loop. These devices, newer to the market, tend to be substantially more complex and costly. The higher resolution density measurement is a step closer to being useful for meaningful emissions detection and mitigation, but a substantial amount of additional functionality must be added externally by the user to interpret the density signal, track and log trends, and communicate decisive information over the user's management network.

Accounting for the impact of temperature variation is of course an important aspect of accurate gas density and therefore accurate gas mass predictions. The operating temperature range for breakers of table 1 is uniformly −40° C. to 40° C. At a nominal pressure of 75 psig at 20° C., this temperature variation corresponds to a −15 psi to +5 psi variation in pressure. Under equilibrium conditions, the temperature compensation is straight forward. However, temperature is rarely expected to be "at equilibrium" in the case of breakers and Gas Insulated Switch (GIS) equipment deployed in outdoor environments across the land. A host of factors including sun, wind, precipitation, and weather in general will drive short-term and diurnal temperature variations which in turn will create temperature gradients across tanks of $SF_6$ gas. Applying the necessary algorithms to effectively compensate temperature dynamics to achieve the desired detection accuracies yet avoid false alarms is a major accomplishment of this invention.

In summary, achieving $SF_6$ detection and mitigation efficiency several orders of magnitude better that current practice, to maintain or improve on current levels of leakage in the face of anticipated global electrical consumption increases, according to the foregoing analyses, requires a 100-fold improvement which in turn implies gas sensor detection sensitivities of 0.5 kg to 1.0 kg reliably achieved over dynamic thermal conditions. The instant invention, achieving the aforementioned detection sensitivity and combining network communications to trigger early service mitigation, brings the 100-fold improvement goal within reach.

Practically speaking, the invention represents an advanced gas sensor that both leverages the advantages of existing technology and applies innovations to overcome its shortcomings with respect to the $SF_6$ emissions mitigation application. It can be globally deployed on breakers and GIS equipment, will accurately track gas additions and losses in real-time, and will be readily integrated into a broad network management infrastructure enabling cost-effective emissions mitigation.

The economic and ecological importance of improved $SF_6$ gas management has been emphasized. In real terms, each of 6.8 billion humans on earth is a stakeholder. The future of his environment, the quality and cost of his electricity, and the cost of all other goods and services he covets (that rely upon electricity) are at stake.

The most immediate beneficiaries of this invention and its technology will be companies that manufacture and sell the advanced sensors it enables. This invention and technology is conceived to be low ingredient cost and designed for manufacturability from inception. Inherently software configurable, it supports flexible optioning and extensible functionality. As to their customers, advanced gas sensor component manufacturers will enjoy the same growing market now shared by conventional gas density switch manufacturers, namely breaker and GIS switchgear OEMs, electric utilities, and other electric substation designers and operators. For example, a manufacturer of gas density switches in North American markets, estimates annual sales over 10,000 units with significant market growth. For the customers' sakes, this invention and technology is conceived to support the surgical detection, tracking, and mitigation of $SF_6$ loss through equipment leakage with products that represent low component and operating cost burdens to the user. The economic benefits are manifold:

Gas expense savings (demand for $SF_6$ and therefore gas costs, already ~$10/lb, is increasing)

Direct process data captured automatically inexpensively demonstrates regulatory compliance, compared to costly, complex, and error prone mass balance procedural alternatives Avoidance of regulatory fines for emissions; and, Capture of offset credits What is the market size for customers that desire these benefits? Based upon a weighted, average nameplate $SF_6$ capacity of 73 kg, and considering global annual $SF_6$ utilization for electric equipment of 5,500 metric tons, and assuming 3 pole tanks per breaker, one can estimate a global population of equipment increasing at approximately 200,000 tanks per year. Assuming this corresponds to a growth rate of 5%, the global established market can be inferred to be approximately 4 million tanks. This is the immediate market for my sensor invention in the upgrade space.

This invention is conceived to be market friendly, utilizing a mechanical bellows technology and form factor well entrenched in the present market. Flexible network interface functionality renders this sensor easy to integrate in the user's network management system.

BRIEF DESCRIPTION OF THE DRAWINGS

FIG. 6 is a left side view of the gas sensor apparatus of FIG. 5.

FIG. 6A is an enlarged portion of FIG. 6.

FIG. 6B is a right side view of the gas sensor apparatus of FIG. 5.

FIG. 10 is a front view of the sensor internal components.

FIG. 10A is front view of the gas sensor apparatus internal components with the riser cutaway illustrating the bellows.

FIG. 10B is an enlargement of a portion of FIG. 10A.

FIG. 26 is a table of gas sensor numerical data.

DESCRIPTION OF THE INVENTION

Figure 1:
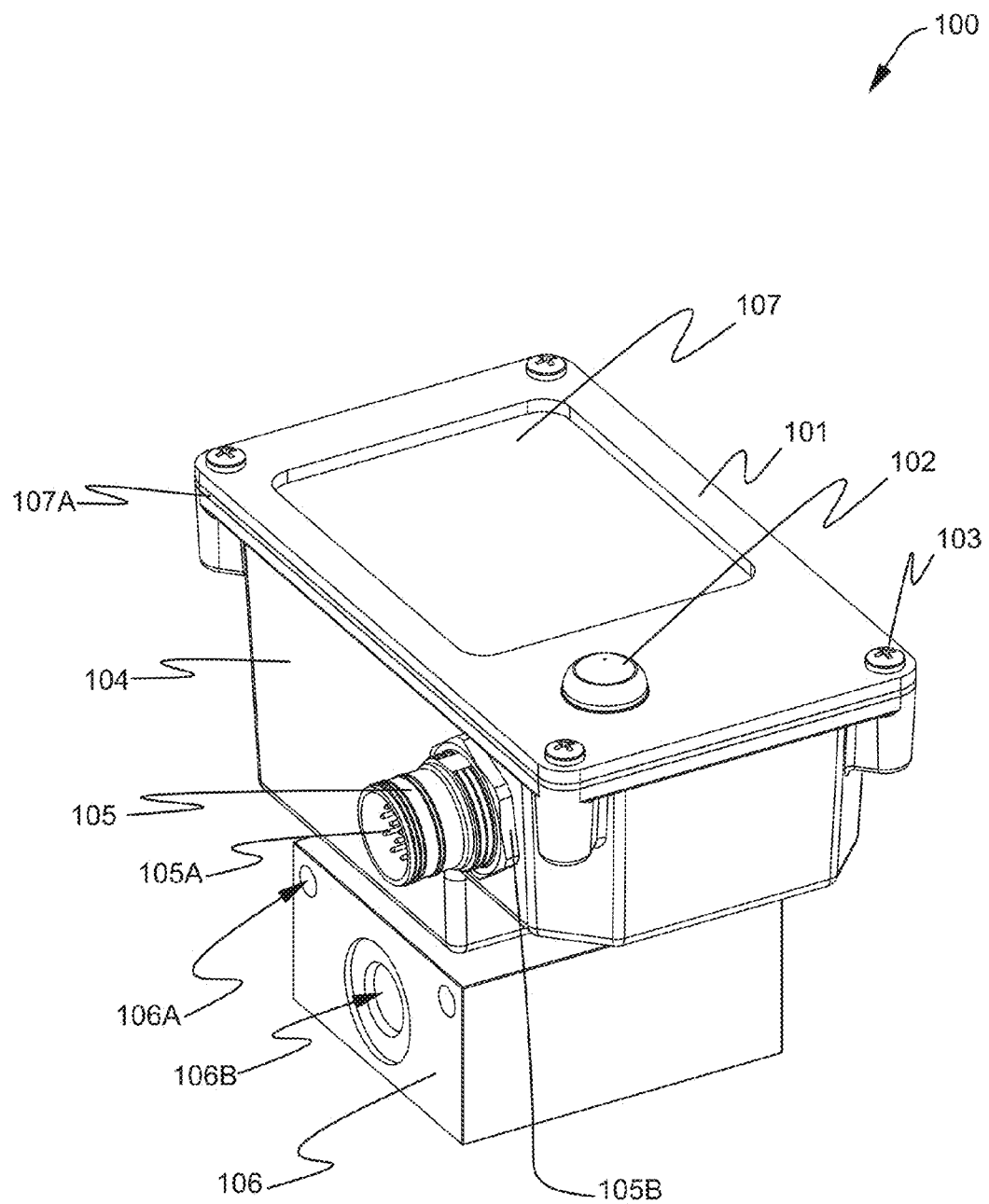
FIG. 1 is a perspective view of the gas sensor apparatus.

As stated above, the instant invention supports a 100-fold reduction in gas emissions. What does this imply for gas density measurement requirements? To address this question, begin by considering that, at a temperature of 20° C., the operating pressure for the breakers of table 1 ranges from 64 psig to 82 psig, a span of 18 psi.

Table 1 also gives the nominal gas mass change attributable to pressure change for each breaker under the aforementioned isothermal conditions. The function is simply proportional to the differential tank volume of the various breakers given the isothermal assumption. As expected, the largest tank represents a worst case requirement for mass sensing resolution since smaller pressure changes accompany larger gas losses (large mass changes). In general, larger tanks will require higher resolution measurements to detect unit changes in gas mass.

TABLE 1

| | Breaker Model Designation | | | | | |
|---|---|---|---|---|---|---|
| | HS | HP-1 | HP-2 | HP-3 | HPI-1 | HPI-2 |
| Rated Maximum Voltage (kV) | 72.5 | 145 | 169 | 242 | 345 | 550 |
| Interrupting Current Rating (kA) | 31.5 | 40 | 40 | 40 | 362 | 40 |
| Tank Volume (cubic meters) | 0.151 | 0.561 | 0.732 | 1.171 | 3.367 | 3.542 |
| SF6 weight at fill pressure (kg) | 5.2 | 19.1 | 24.9 | 39.9 | 114.8 | 120.7 |
| SF6 weight at nominal (kg) | 4.7 | 17.4 | 22.7 | 36.3 | 104.3 | 109.8 |
| SF6 weight at alarm (kg) | 4.3 | 16.0 | 20.9 | 33.4 | 96.1 | 101.1 |
| SF6 weight at lockout (kg) | 4.0 | 14.8 | 19.3 | 31.0 | 89.0 | 93.6 |
| SF6 Emission between fill and alarm (kg) | 0.8 | 3.1 | 4.1 | 6.5 | 18.7 | 19.7 |
| SF6 mass per unit pressure (kg/psi) | 0.063 | 0.232 | 0.302 | 0.484 | 1.391 | 1.464 |
| Distribution frequency[12] | 50% | 14% | 13% | 15% | 6% | 2% |

Table 1—Representative gas insulated breakers with OEM recommended SF6 fill conditions. If filled to just below fill capacity, breaker type HPI-2 would emit 19.7 kg of SF6 before the alarm threshold would trigger. Typically the so-called "nameplate capacity" will be three times larger than the above tank capacity since the breaker comprises three phases each with its individual tank The approximate frequency with which various sizes occur in practice is attributable from Blackman.

Now the question arises, what is the magnitude of gas loss one needs to begin detecting? SF6 emission rates studied by various methods to date appear to place gas emissions in the range of 5% to 10% of total nameplate capacity annually. Accounting for frequency of distribution of breakers by voltage rating (and therefore by tank size), the weighted average of the nameplate capacities is approximately 73 kg (remember—3 tanks per breaker typically). In a study of 2,329 breakers by Blackman, 170 (7.3%) were found to be leaking. The amount of gas emitted to atmosphere annually may thereby be estimated at 3.7 kg to 7.3 kg per breaker (5% to 10% of 73 kg). The actual leaks arise from the aforementioned 7.3% of the breaker population. Therefore, the average leakage amount per leaking breaker is on the order of 50 kg to 100 kg annually.

The sensor-gas interface mechanism as one component of the advanced gas sensor has many important aspects. The use a mechanical bellows approach is utilized for several reasons. These reasons include the bellow's simplicity, reliability, and broad use in $SF_6$ gas density switch applications. The use of a mechanical bellows leads to a requirement for detecting and processing mechanical displacement information. Processing the displacement information supports accurate gas pressure inferences.

The advanced gas sensor combines a bellows sensing element with an MCU Electronics module comprising electronics and software for acquiring raw displacement and temperature information and processing these into accurate measurements.

Reliable pressure and temperature readings must ultimately be rendered from raw sensor data. The present invention utilizes an efficient signal processing chain for this purpose. Noise, stability, and other potential problems are thereby identified and overcome.

Processed pressure and temperature readings must be interpreted to predict gas density which in turn predicts gas mass changes in light of known, rigid tank volumes. The process, in isothermal conditions, is relatively straight forward. Under conditions of changing temperature, the process becomes more challenging. Ideal gas law and virial equations with alternative techniques for calculating temperature dependent coefficients form the foundations of the algorithms utilized for this purpose.

As stated earlier, the present invention uses a mechanical bellows approach to gas interface and pressure sensing. The advantages of this choice are described above. Mechanical bellows components are readily available from a variety of sources including Solon Manufacturing of Chardon, Ohio Mechanical bellows are widely used in mechanical, gas density monitoring products that enjoy a dominant share of the North American alarm-monitoring market.

The bellows expands under increasing pressure. In the configuration of the embodiments set forth herein, the bellows actuates a rigid coupling to a platen. The platen's starting position and translational gain are simultaneously adjusted with a counter-biasing coil spring. Nominal gain in the range of 0.001" platen deflection per 1 psi change is typically achieved.

In the mechanical density monitor application, the platen carries bi-metal elements that in turn actuate snap-action micro-switches under conditions of sufficient displacement. The bi-metal elements provide a mechanical temperature compensation mechanism.

Figure 16:
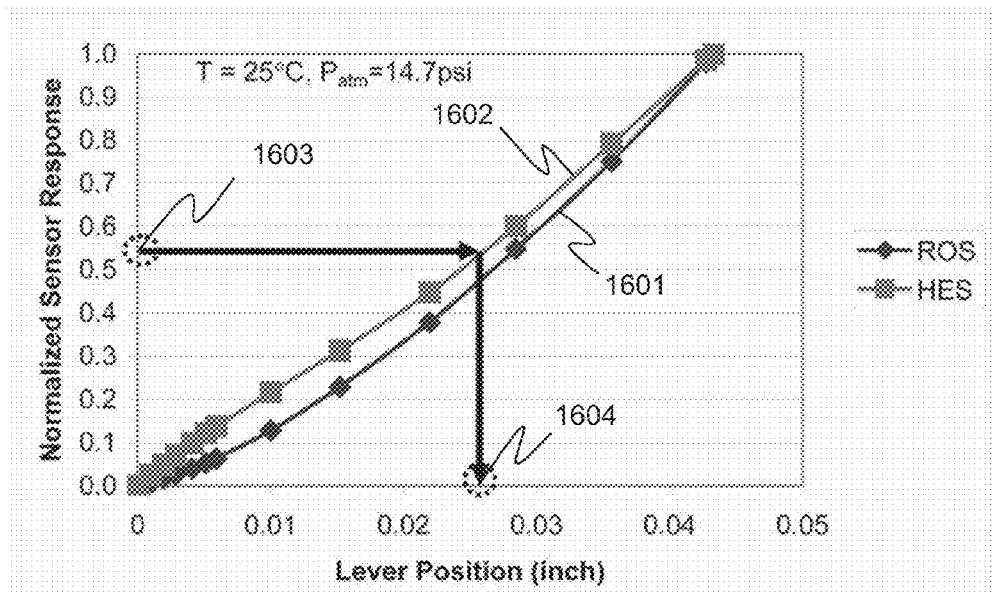
FIG. 16 is a normalized sensor response as a function of lever position.

Contrastingly, in the instant invention, the platen is adapted to carry displacement sensor components which take the form of reflective surfaces, magnets, and other components supporting displacement detection alternatives. FIG. 16 shows the normalized sensor response of an embodiment which utilizes an infrared reflective object sensor (ROS) and another embodiment that uses a Hall Effect sensor (HES). FIGS. 6, 6A, 9, 10, 10A, 10B, and 12A show the mechanical aspect of embodiments using the reflective object sensor and Hall effect sensor components respectively.

As stated above, the invention targets supporting a 100-fold reduction in gas emissions. In the discussion above, it was deduced that a 100-fold improvement in emissions mitigation implies gas sensor sensitivities of 0.5 kg to 1.0 kg. According to table 1 above, this suggests a differential pressure resolution on the order of 16 psi to 0.35 psi. Recall that the operating span of interest is approximately 18 psi. Thus the required pressure measurement resolution (before correction) is in the range of 1 part in 1.2 to 1 part in 52.7. In digital measurement terms, this corresponds to a 1 bit to 6 bit dynamic range, which is achieved using a microcontroller and 12 bit analog to digital converters.

Core bellows devices, prior to any modification, have been bench tested for displacement response over the pressure range of interest at 20° C. Conventional gauge room equipment was used to measure displacement. Regulated compressed air provided pressure actuation. Pressure gradients in both directions have been utilized to quantify hysteresis, and several runs are made to assess short-term repeatability. Analysis of data captured in these tests was analyzed and definitively demonstrates the bellows fitness for the application in this invention as shown hereinbelow.

Figure 13:
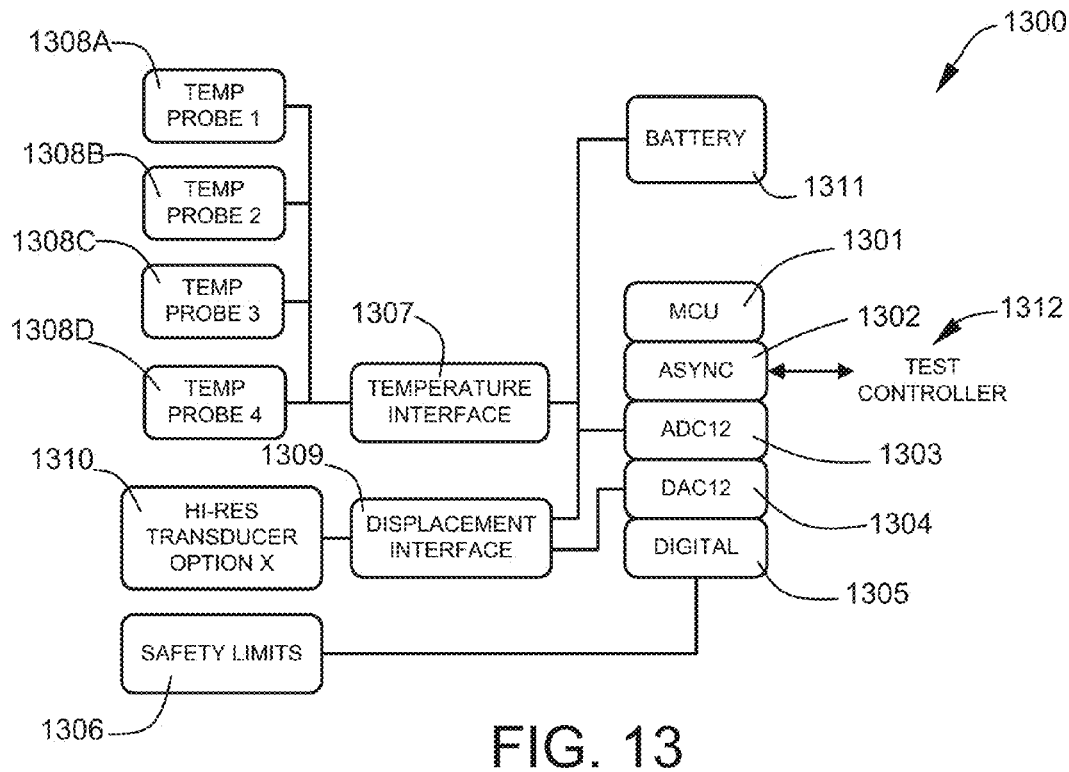
FIG. 13 is a hardware block diagram.

A microcontroller 1301 is used to perform displacement sensing and temperature sensing, and to communicate raw data to the other controller functions (via asynchronous serial communications initially). FIG. 13 is a simplified block diagram of the MCU 1301 and its interactions with the other elements of the invention. The Hi-RES transducer 1310 can optionally be the aforementioned infrared reflective object sensor (ROS), Hall Effect sensor (HES), or other displacement transducer. The temperature probes can be thermistors 507B, 507D, 617B, 617D, thermocouples, RTD, or other suitable temperature transducers. FIG. 13 illustrates, diagrammatically, temperature probes 1308A, 1308B, 1308C, 1308D located within the sensor housing. Reference numerals 1308A-D indicate, generically, many different types of temperature probes which may be used. FIG. 13 also illustrates the battery 1311, a temperature interface 1307, a displacement interface 1309, as well as a test controller (network manageable controller) 1312, a communication subsystem 1302, an analog to digital controller 1303, and a digital to analog controller 1304, a digital I/O interface subsystem 1305, and a safety limit detection subsystem 1306.

MCU subsystem modularity allows easy substitution of alternative circuits for the powered by battery DISPLACEMENT INTERFACE 1309 and HI-RES TRANSDUCER 1310. The MCU 1301 monitors battery state of charge and computes circuit power consumption as well, an important distinguishing characteristic of circuit and algorithmic alternatives. The FLASH memory based MCU 1301 may be conveniently reprogrammed to adapt to varying sensing requirements. Operating parameters may be programmed and acquired data retrieved over the bidirectional, asynchronous communications interface.

Initial choices for HI-RES TRANSDUCER 1310 used to measure platen 601 displacement include Hall Effect and photo diode/transistor technologies. The optical alternatives comprise both transmission and reflective technologies. Piezo strain gauge and ultrasonic systems are possible as well.

Processing and calibration requirements for rendering accurate pressure readings from displacement data are included. Temperature channels are also logged during operation. All data generated by the displacement and temperature measurement blocks is forwarded to the Temperature and Pressure Processing blocks. The invention covers the operating and temperature ranges of interest. Temperature gradient and leak rate tests are also satisfied. The invention includes the signal processing necessary for rendering reliable pressure and temperature readings from raw displacement and temperature sensor data.

Figure 14:
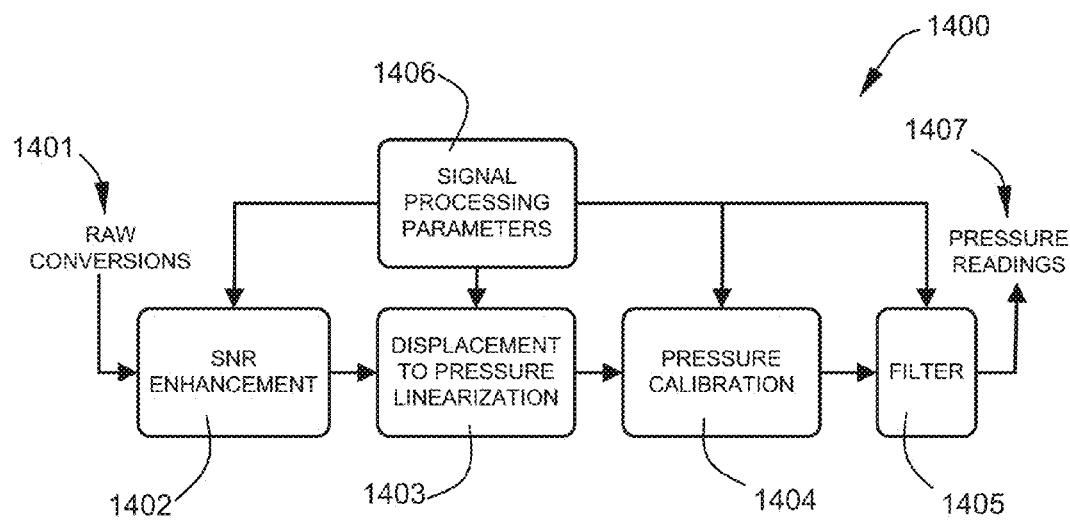
FIG. 14 is a processing block diagram.

FIG. 14 is a processing block diagram 1400 which illustrates the general topology for processing displacement data. A similar signal chain is utilized for temperature data. The order of the functions utilized is based upon the characteristics of the raw data and the desired resolution and accuracy of the processed readings. Reference numeral 1401 signifies raw conversions from displacement and temperature subsystems which are input into a system which enhances the signal to noise ratio. Reference numeral 1403 signifies a system which linearizes the displacement to pressure calculation. Reference numeral pressure calibration signifies a pressure calibration system and reference numeral 1405 signifies a digital filtering subsystem. Reference numeral 1406 signifies signal processing parameters which are included in the signal to noise ration subsystem and the linearization of displacement into pressure. Reference numeral 1407 signifies pressure readings output to gas mass calculations and user interfaces.

Figure 15:
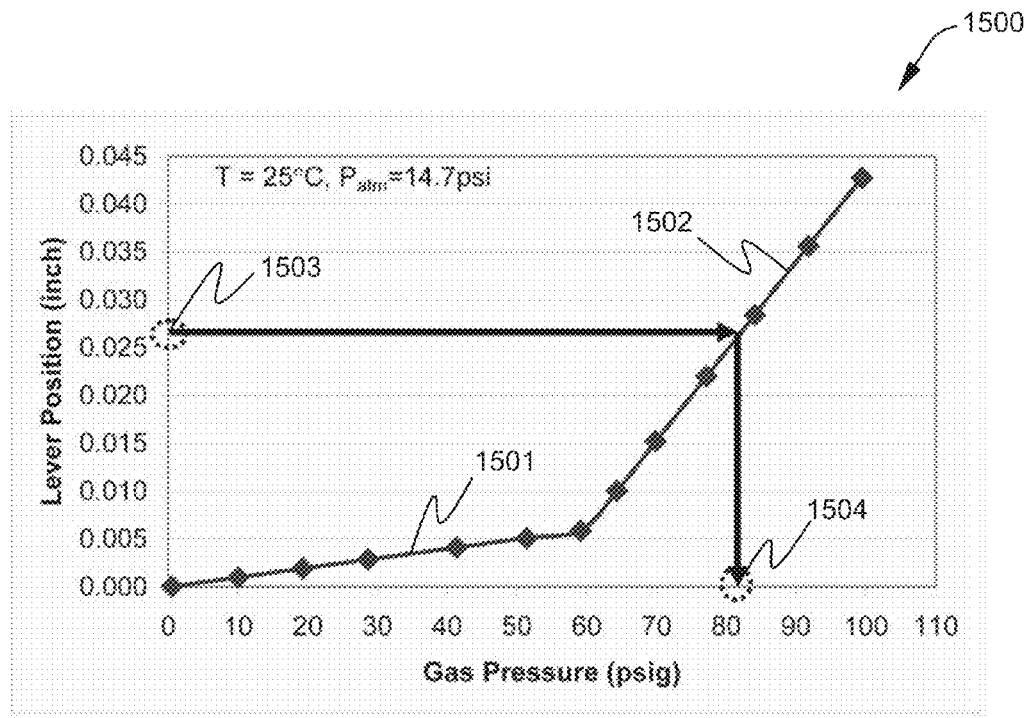
FIG. 15 is a graph lever position as a function of gas pressure at 25° C.

FIG. 15 is a graph lever position 1500 as a function of gas pressure at 25° C. Reference numeral 1501 indicates the lever response from 0 psig to 60 psig. It will be noticed that line 1501 represents the displacement of the lever with respect over pressure range of 0 to 60 psig and with the lever acting against the ball nose spring plunger. Reference numeral 1502 is a line on the graph of the lever position from 60 to 100 psig for the coil spring 608 and bimetal hinge 708. Reference numeral 1503 is a particular lever position of 0.026" corresponding to a pressure 1504 of 81 psig.

FIG. 16 is a normalized sensor response 1600 as a function of lever position at 25° C. FIG. 16 is a normalized sensor response 1600 as a function of lever position. Reference numeral 1601 is the response of reflective object sensor and reference numeral 1602 is the response of Hall effect sensor (HES). Reference numeral 1603 is a particular HES response of 0.55 corresponding to a particular lever position 1604 of 0.026".

N.B. Calibration is achieved entirely using digital techniques to determine coefficients stored onboard in nonvolatile memory. Use of precision or adjustable components is avoided in favor of standard tolerance, inexpensive, high stability components.

An equation of state model is required to compute the target gas density from calibrated temperature and pressure data. A first order Gas Density Model is used and provides satisfactory results in many cases.

The well known virial form set forth below as equation 2 utilizing coefficient functions for $SF_6$ selected from various perspectives is an alternative embodiment:

$$\frac{pV}{nRT} = 1 + B(T)\frac{n}{V} + C(T)\frac{n^2}{V^2} + \ldots \quad (2)$$

Where p, V, n, R, and T have their usual meanings in the ideal gas law, and B(T) and C(T) are the second and third virial coefficients respectively, each non-linear functions of temperature T.

This step further draws upon recent work by Scalabrin describing a computationally efficient neural network technique for computing coefficients in a certain form of state equation.

It is an important aspect of the instant invention to use a micro-power microcontroller platform to sense gas density to sufficient accuracy to discern 0.5 kg emission events under a range of conditions of interest for the largest tank volumes expected.

FIG. 1 is a perspective view 100 of the gas sensor apparatus. Cover 101 and liquid tight pushbutton 102 are shown in FIG. 1. Cover 101 is affixed to housing 104 by cover retaining screws 103. Sensor connector 105 provides communications between the gas sensor apparatus and the exterior of the switchgear control cabinet. Power to the apparatus is also supplied through the connector pins 105A. Connector nut 105B affixes the connector to the housing 104. Manifold block 106 includes a first gas port 106B for admission of gas to the gas sensor apparatus. Manifold block bolt hole 106A includes bolts which secure the manifold in place. A display deadfront 109 (display cover) and gasket 107A are illustrated.

Figure 2:
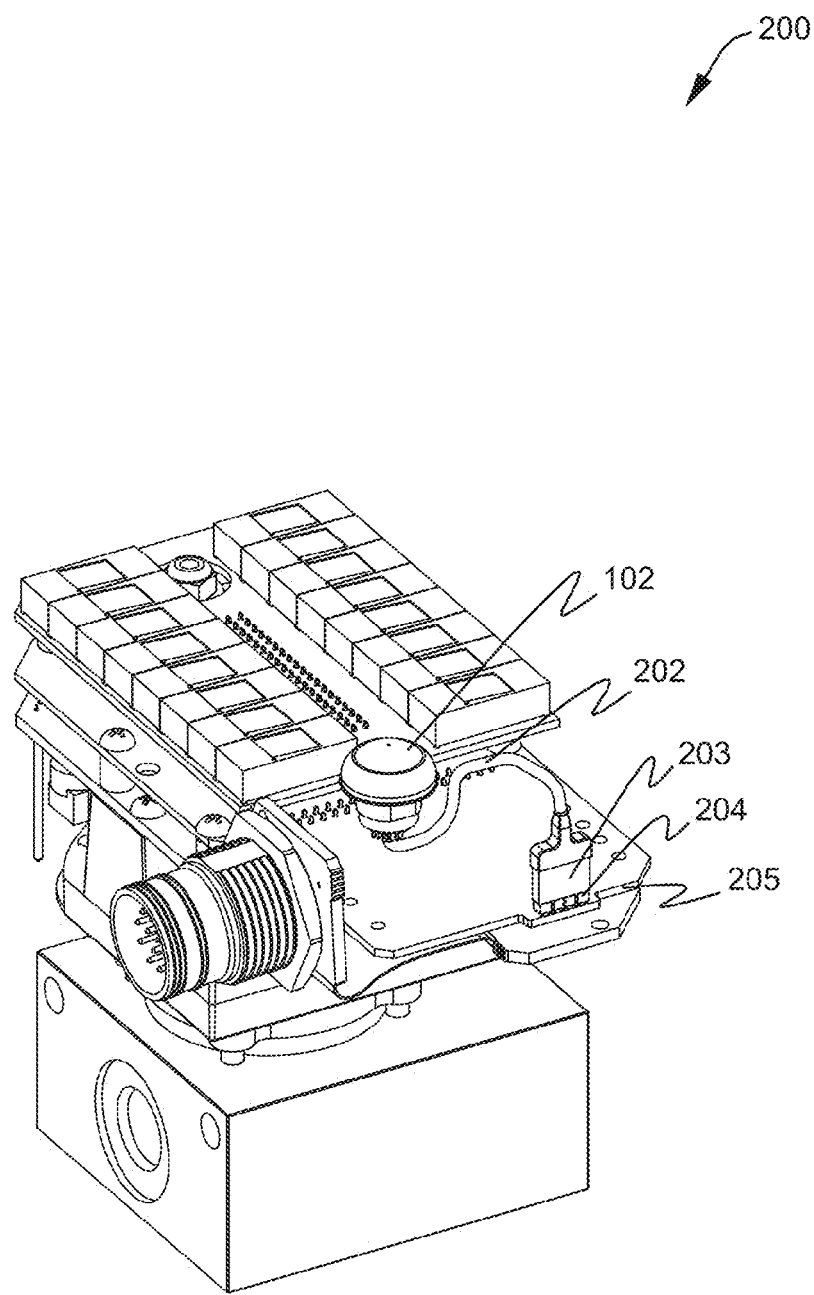
FIG. 2 is a perspective view of the gas sensor apparatus with covering and housing removed.

FIG. 2 is a perspective view 200 of the gas sensor apparatus with covering 101 and housing 104 removed. Liquid tight pushbutton 102 when depressed provides a temperature compensated pressure readout. Pushbutton cable 202 and connector 203 enables electrical communication between the pushbutton and the electronics on board the gas sensor apparatus. Connector 203 interconnects with processor PCB pushbutton connector 204. Processor printed circuit board 205 is illustrated in FIG. 2.

Figure 3:
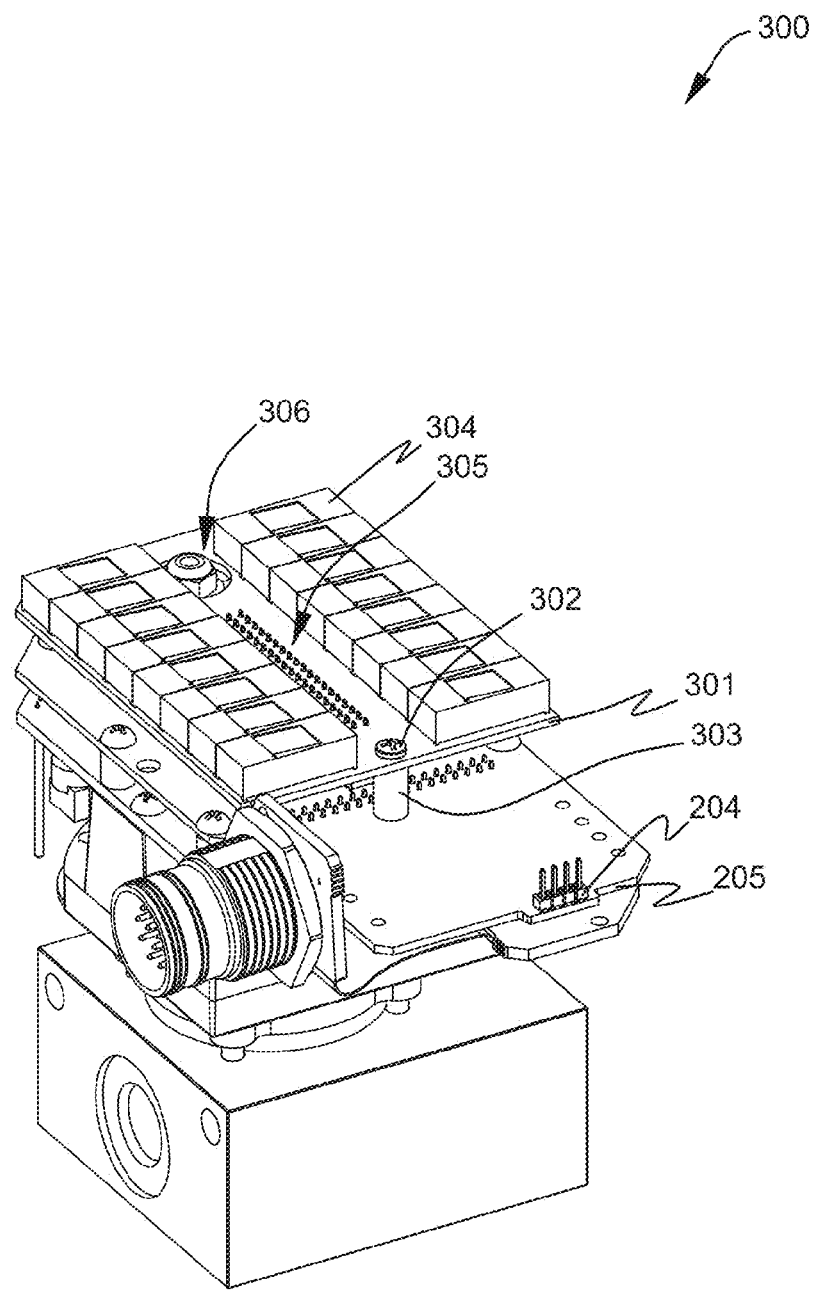
FIG. 3 is a perspective view of the gas sensor apparatus similar to FIG. 2 with the pushbutton removed.

FIG. 3 is a perspective view 300 of the gas sensor apparatus similar to FIG. 2 with the pushbutton removed. Display printed circuit board 301 is illustrated as being mounted to the processor printed circuit board 205 using a standoff (spacer 303) and screw 302. Display digits 304 communicate a temperature compensated pressure readout (display). In the approximate middle of the printed circuit board 301, are processor printed circuit board connectors. The display printed circuit board includes a coil spring clearance hole 306.

Figure 4:
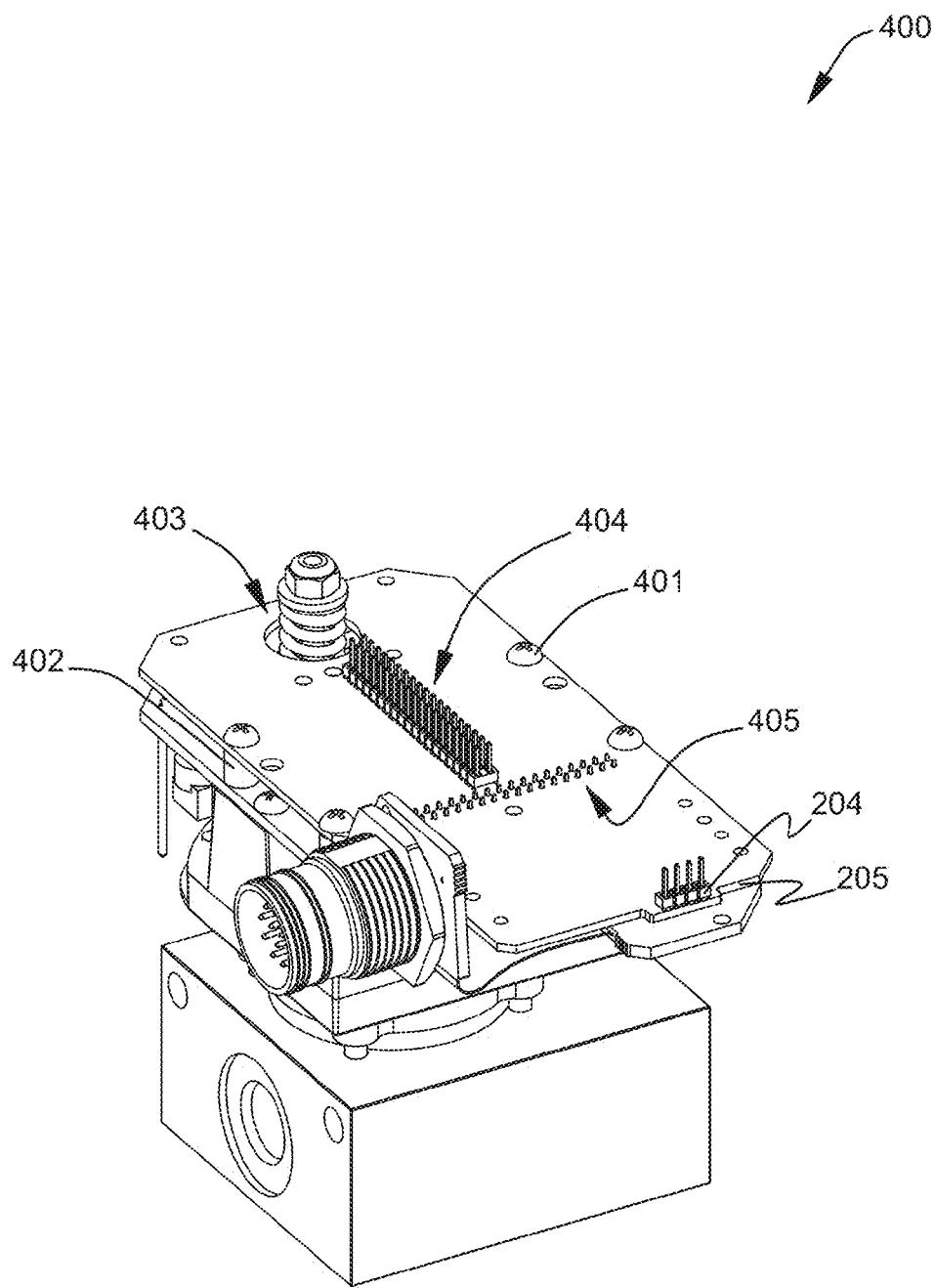
FIG. 4 is a perspective view of the gas sensor apparatus similar to FIG. 3 with the temperature sensors and their mounting plate removed.

FIG. 4 is a perspective view 400 of the gas sensor apparatus similar to FIG. 3 with the display printed circuit board removed. The temperature sensors 1308A-D, are best viewed, diagrammatically in FIG. 13. The temperature sensors will be located in the sensor housing in various places so as to obtain accurate temperature readings representative of the gas being measured. A typical gas used in switchgear is sulfur hexafluoride gas ($SF_6$). $SF_6$ plays a crucial arc-suppression role in this equipment. Other gases may be used in the switchgear. Further, this invention is equally applicable to the determination of loss of any gas from any containment structure. As described in further detail hereinbelow, the loss of gas is determined by a change in the temperature compensated pressure.

Figure 7:
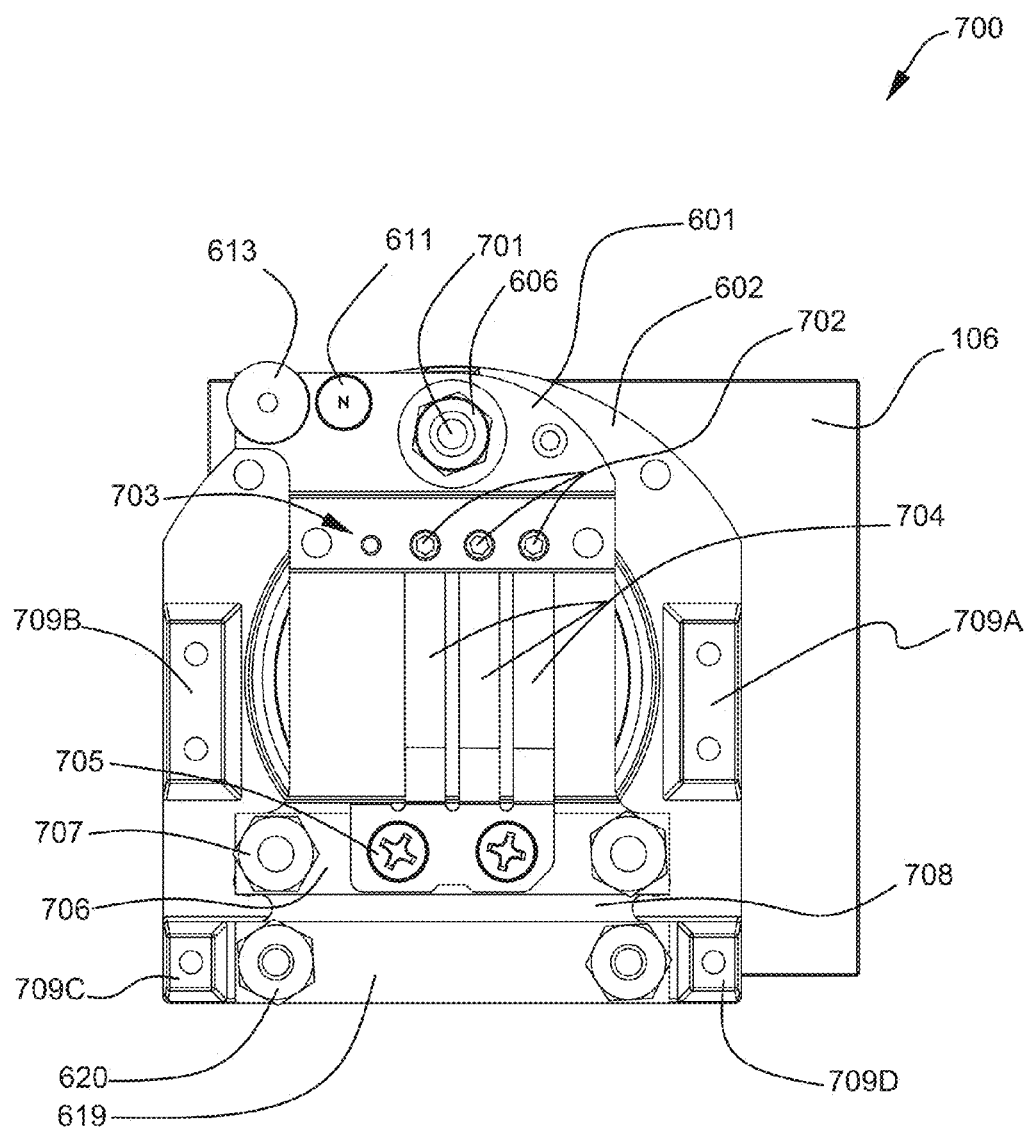
FIG. 7 is a top view of the of the gas sensor apparatus as illustrated in FIG. 6 with the printed circuit board removed illustrating the lever and switch.
Figure 11:
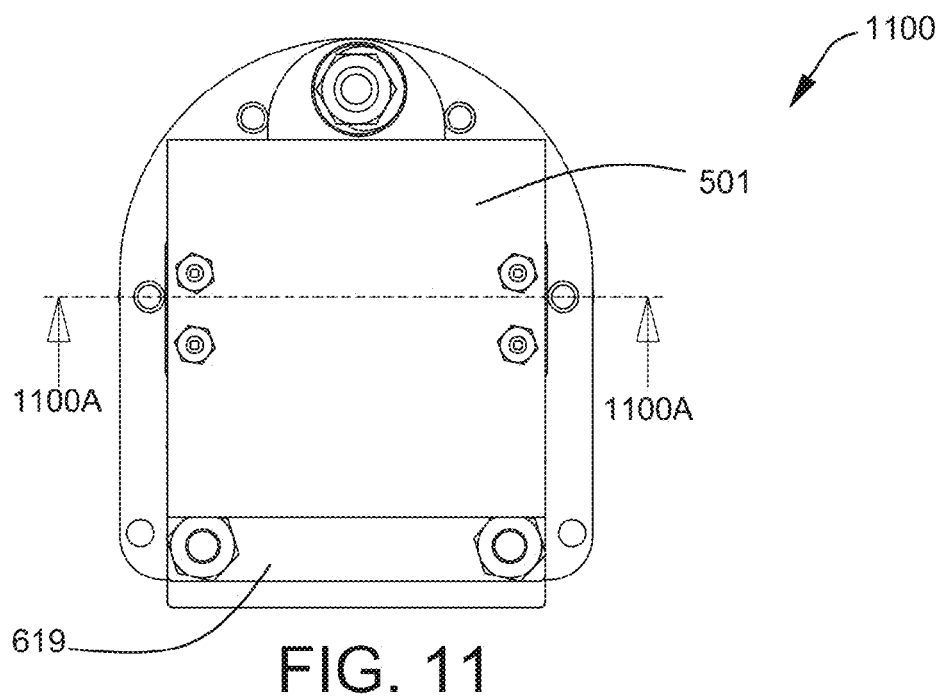
FIG. 11 is a top view of gas sensor apparatus internal components.
Figure 11A:
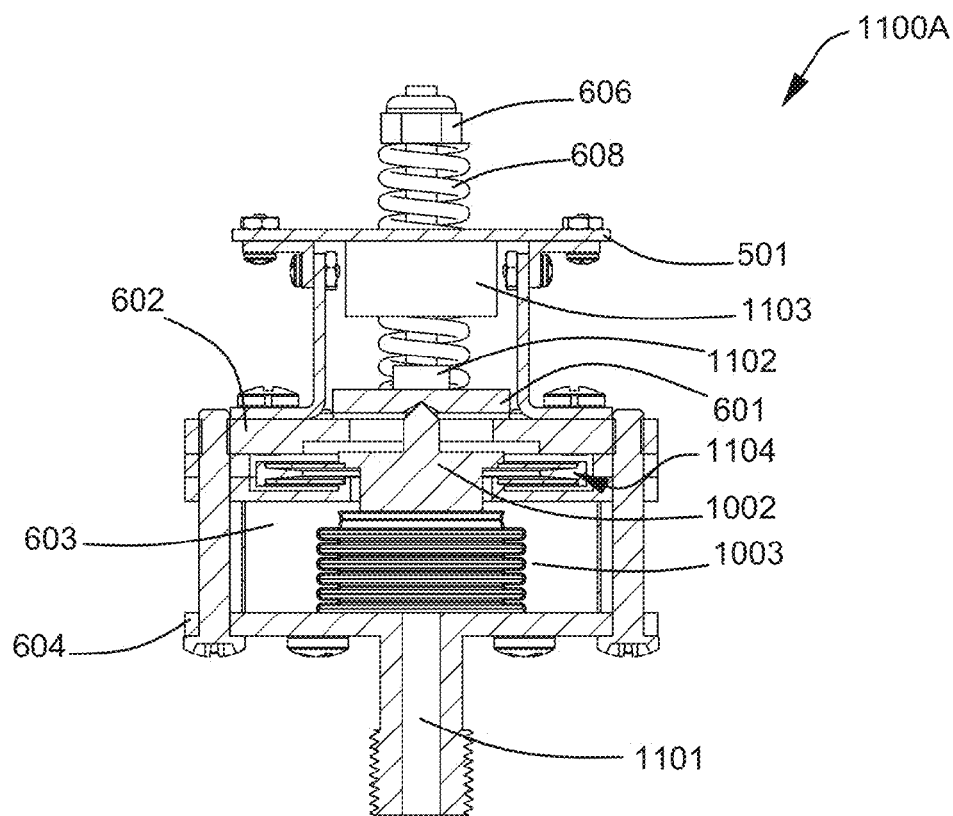
FIG. 11A is a cross-section of FIG. 11.
Figure 12:
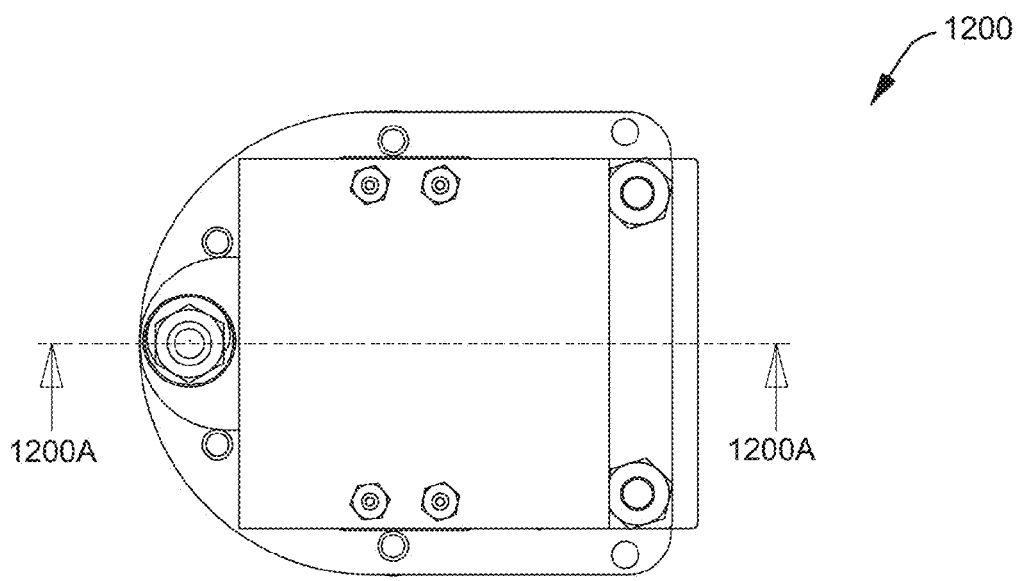
FIG. 12 is a top view of the gas sensor apparatus internal components.
Figure 12A:
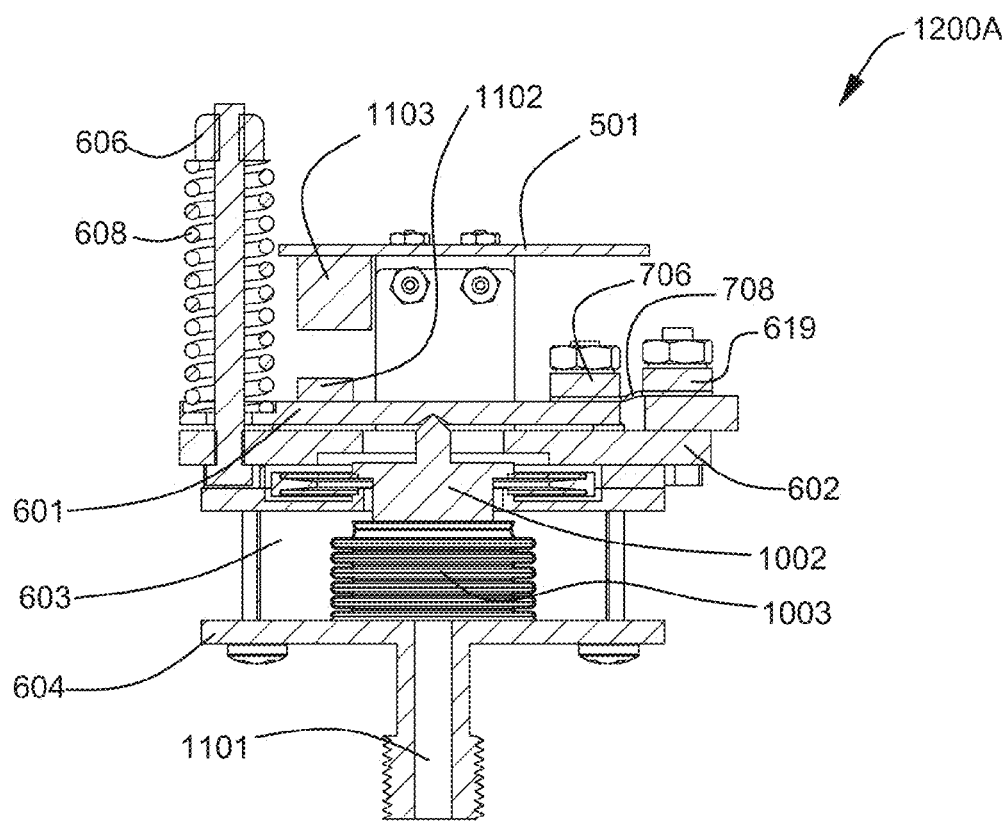
FIG. 12A is a cross-sectional view of the gas sensor apparatus of FIG. 12.

Referring to FIGS. 11, 11A, 12, and 12A, some of the important internal elements of the invention are disclosed. FIG. 11 is a top view 1100 of gas sensor apparatus internal components. FIG. 11A is a cross-section view 110A of FIG. 11. FIG. 12 is a top view 1200 of the gas sensor apparatus internal components. FIG. 12A is a cross-sectional view 1200A of the gas sensor apparatus of FIG. 12. Switch printed circuit board 501 includes a microcontroller unit 1103, 1301. Base plate 602 is affixed to the adapter flange 604 by unnumbered screws. Lever 601 pivots about a pivot portion (unnumbered) of the coupling 1002 of the bellows 1003. Stabilizers 1104 of the coupling 1002 tend to center the coupling 1002 of the bellows as the bellows is raised and lowered in response to pressure within the bellows. Gas port 1101 communicates gas into the bellows 1003. Riser 603, adapter flange 604, base plate 602 provide a foundation for operation of the lever 601. Lever 601 pivots about coupling 1002. Bimetallic strip 708 (element) is affixed to the lever 601 by retaining plate 706. Bimetallic strip 708 is also affixed to an unnumbered block by retaining plate 619. FIG. 7 illustrates the bimetallic strip 708 and notches cut therein for desired performance thereof. The material of the bimetallic strip 708 is not limited in this specification. The bimetallic strip functions to compensate for the influence the temperature of the gas has on gas pressure.

One important object of the invention is to determine if gas is being loss from the switchgear. The gas sensor apparatus operates over a wide range of temperature and pressure conditions other than standard temperature and pressure conditions. If pressure of the gas rises, but the mass of the gas within a known volume stays the same (ie no loss occurs), then the apparent pressure in the volume (tank) appears to increase. The bimetallic strip 708, however, adds a downward force on lever 601 to counteract the additional force of the gas within the bellows due to an increase in gas temperature. If pressure of the gas decreases, but the mass of the gas within a known volumes stays the same (ie no loss of gas occurs), then the apparent pressure in the volume (tank) appears to decrease. In a similar manner, an apparent decrease in gas pressure due to a relatively low temperature is compensated by an upward force on lever 601 to counteract the reduction in force of the gas within the bellows due to a decrease in gas temperature.

A magnet is affixed to the lever 601. A reflective surface is also affixed to the lever 601. A Hall Effect sensor is applied to the switch printed circuit board 501. A reflective object sensor is affixed to the switch printed circuit board. In FIG. 12A, reference numeral 1102 is being used to denote the magnet and the reflective surface. In FIG. 12A, reference numeral 1103 is being used to denote the Hall Effect sensor, the reflective object sensor and the processor module.

Figure 9:
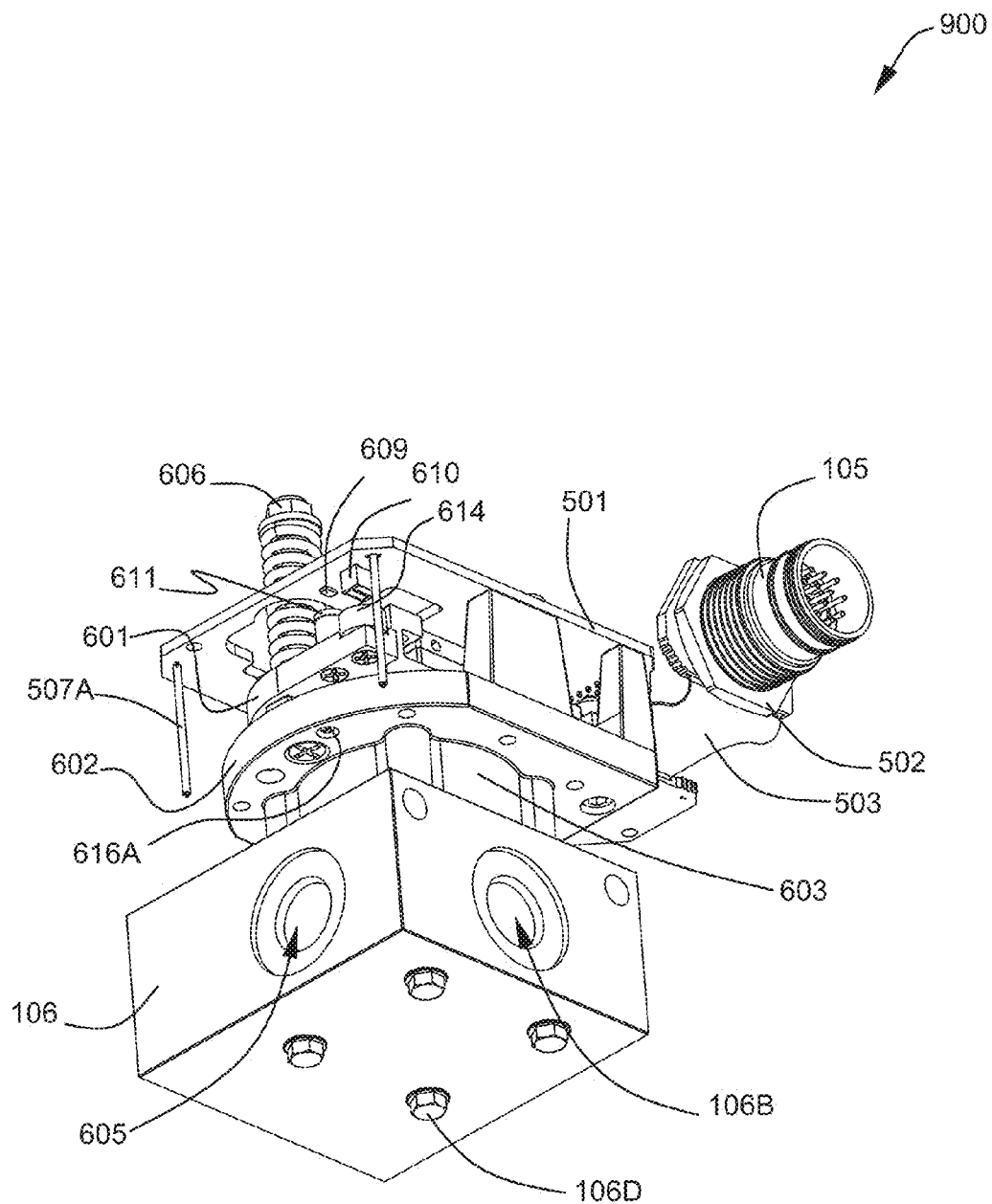
FIG. 9 is a bottom perspective view of the gas sensor apparatus.

FIG. 9 is a bottom perspective view 900 of the gas sensor apparatus. Hall Effect sensor 609 and reflective object sensor 610 are illustrated in FIG. 9 on the underside of switch printed circuit board 501. Magnet 611 and reflective surface boss 614 are illustrated residing on lever 601. Lever 601 moves vertically with a small amount of pivotal movement as well as can be visualized in FIG. 12. As lever 601 moves, the Hall Effect sensor 609 and the reflective object sensor 610, detect the movement. Processor 1301 is not visualized in FIG. 9, but it can reside on the underside of printed circuit board 501 as illustrated in FIG. 12A. Alternatively, processor 1301 can be located on the upper or top side of printed circuit board 501.

Referring to FIG. 13, processor 1301 receives temperature inputs from temperature probes within the sensor housing and processes the various temperature signals for further evaluation of the pressure information received from the high resolution displacement transducers 1310. Reference numeral 1310 indicates that "OPTION X" displacement transducer(s) may be used. This means that one or both of the Hall Effect sensor and/or the reflective object sensor may be used in the calculation of movement of the lever. It also means alternative displacement or distance sensing technologies including capacitive, sonic, inductive, or other well known technologies may be used singly or in combination. Movement of the lever in combination with the use of temperature data, determines the gas density. In this patent application, various parameters are expressed by the ideal gas law stated above.

$$pV = nRT \therefore \frac{n}{V} = \frac{p}{RT}$$

Where P is gas pressure in the system, V is the volume of gas which is fixed by the equipment's rigid tank, R is a constant, T is temperature, and n is the mass quantity of gas. With V and R constant, measuring P and T determines n/V, the gas density.

Figure 8:
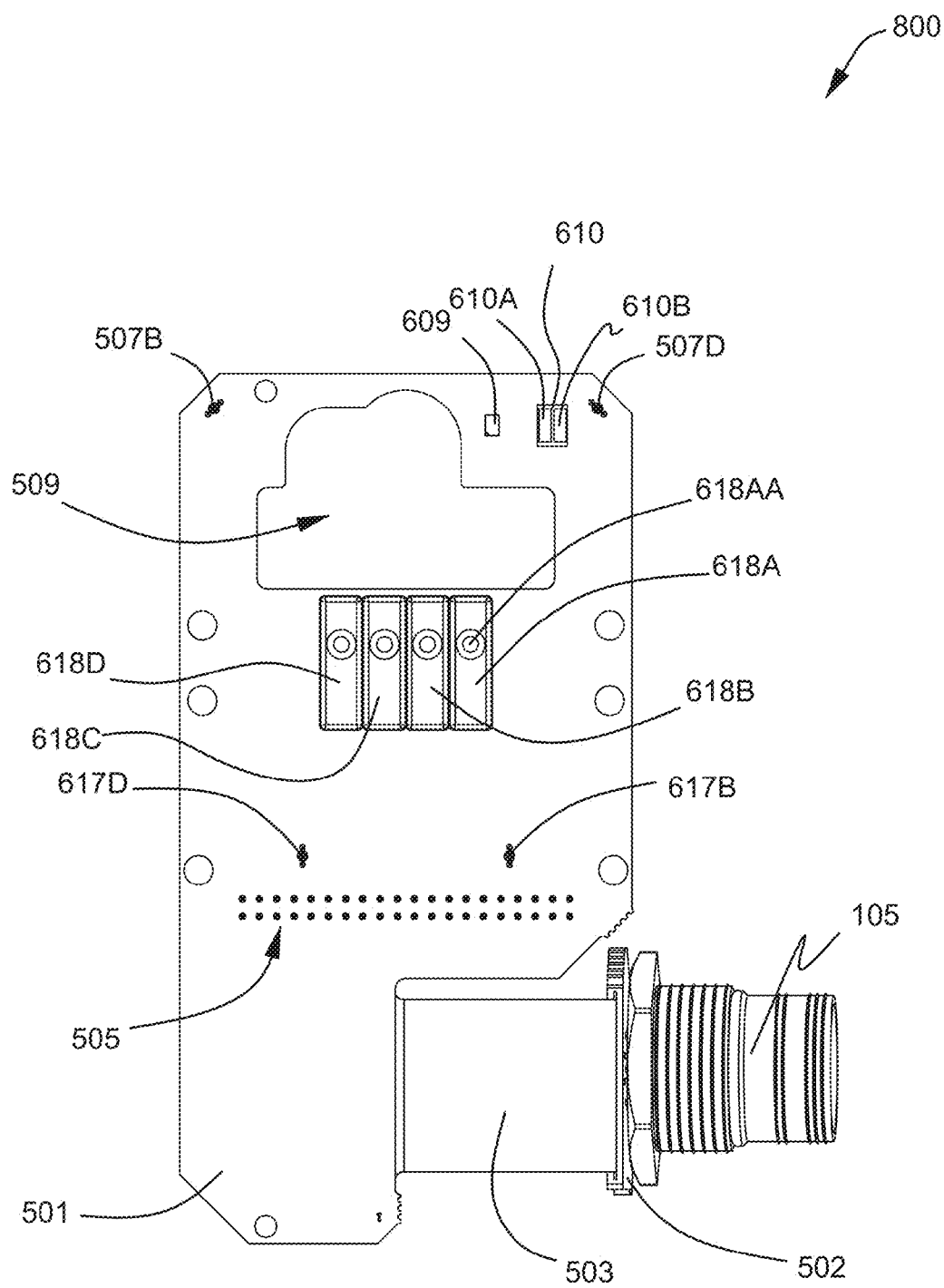
FIG. 8 is a bottom view of the printed circuit board.

The gas sensor apparatus includes switch actuator elements 704 which reside on lever 601 which engage the actuators 618AA of snap action switches 618A-D as illustrated in FIG. 8. FIG. 8 is a bottom view 800 of the printed circuit board 501. Switches 618A, 618B, 618C and 618D protrude downwardly from printed circuit board 501. Each switch includes an actuator 618AA although only one such actuator is labeled with reference numeral 618AA. When the actuator elements 702 engage the actuators 618AA, then contacts within the switch are electrically joined or completed which results in an alarm, warning, or other signal sent to a user. These switch functions include the temperature compensation provided by the bimetallic strip. Hall Effect sensor 609, reflective object sensor 610, reflective object sensor phototransistor 610A, and reflective object sensor infrared LED emitter 610B are illustrated in FIG. 8.

Figure 8A:
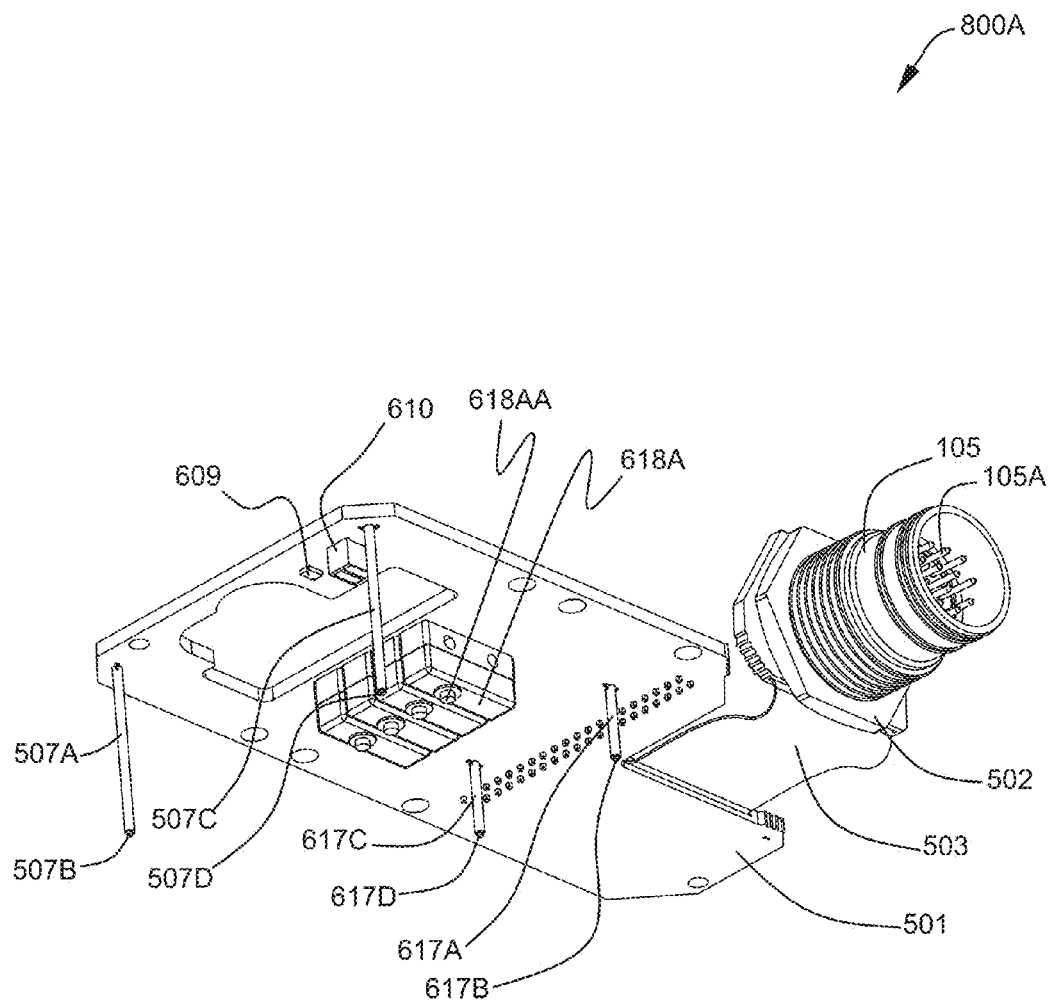
FIG. 8A is a bottom perspective view of the printed circuit board.

FIG. 8A is a bottom perspective view 800A of the switch printed circuit board 501 wherein the sensor connector 105 and the sensor connector contact pin 105A are illustrated along with the printed circuit board 501. Connector support 502 is affixed to PCB flexible circuit element 503. First 507B and second 507D thermistors are illustrated in FIG. 8A as are third 617B and fourth 617D thermistors. First thermistor stalk 507A and second thermistor stalk 507C are illustrated well in FIG. 8A. Third thermistor stalk 617B and fourth thermistor stalk 617C are illustrated well in FIG. 8A.

Figure 5:
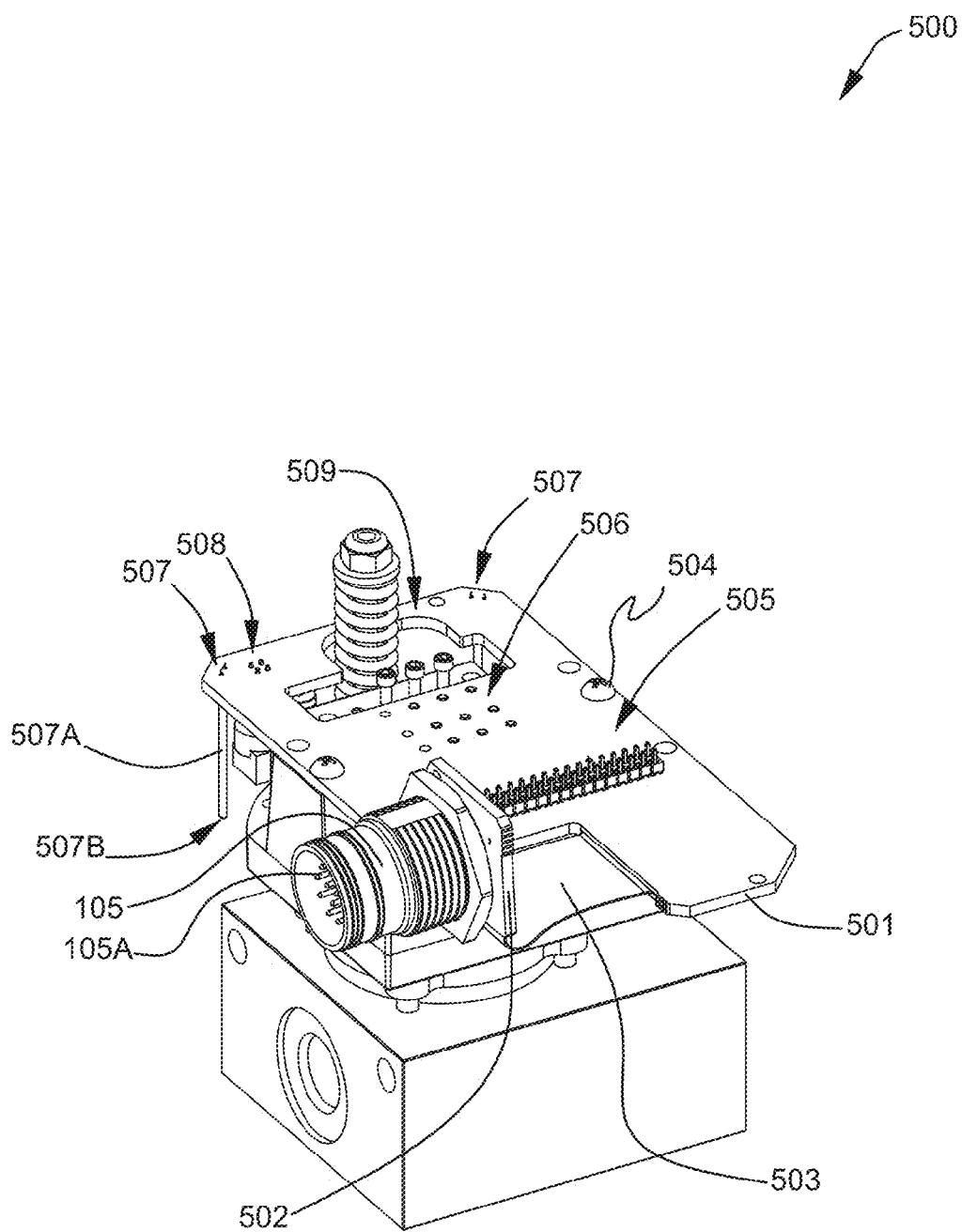
FIG. 5 is a perspective view of the gas sensor apparatus similar to FIG. 4 with the processor printed circuit board removed.

FIG. 5 is a perspective view 500 of the gas sensor apparatus similar to FIG. 4 with the processor printed circuit board 205 removed. Reference numeral 501 is the switch printed circuit board and reference numeral 502 is the switch printed circuit board connector. Flexible circuit element 503 is interconnects the connector 502 to the switch printed circuit board 501. Screws 504 retain the printed circuit board to the main structure of the apparatus. Switch connections 506 are viewed in FIG. 5 and enable attachment of the snap-action switches from the bottom side of the printed circuit board 501. The bottom side of printed circuit board is best viewed in FIGS. 8 and 8A. Each of the switches 618A-D is actuated by spring loaded metallic actuator elements 704 best viewed in FIG. 7. The spring loaded actuator elements 704 are very slightly bowed depending on the amount of adjustment 702 which bias the elements 704 and, therefore, control the actuation of the switches. The spring loaded elements 704 are affixed to bimetallic hinge retaining plate 706. Still referring to FIG. 7, the reflector 613, the magnet 611, and the spring stud 701 are illustrated.

FIG. 7 is a top view 700 of the of the gas sensor apparatus as illustrated in FIG. 6 with the printed circuit board 501 removed illustrating the lever 601 and switch actuator elements. Manifold block 106, lever 601, base plate 602, coil spring nut 606, spring stud 701, switch PCB mounting bosses 709A-D, 611 magnet, reflective surface 613, bimetal hinge base retaining plate 619, bimetal hinge base retaining plate nut 620, switch actuator element adjuster screws 702, switch actuator elements 704, switch actuator elements flange screw 705, bimetal hinge lever retaining plate 706, bimetal hinge lever retaining plate nut 707 and bimetal hinge 708 are all well illustrated in FIG. 7.

Referring to FIG. 5 again, thermistor 507A, thermistor stalk 507B and thermistor connections 507 are illustrated. Further, the connection 508 for the reflective object sensor and the cutout 509 for the coil spring are shown.

FIG. 6 is a left side view 600 of the gas sensor apparatus of FIG. 5. FIG. 6 illustrates manifold block 106, switch PCB 501, switch PCB processor PCB connector 506, first thermistor stalk 507A, first thermistor 507B, third thermistor stalk 507C, and third thermistor 507D. Lever 601, base plate 602, riser 603, and adapter flange 604 are illustrated in FIG. 6. Second gas port 605, coil spring nut 606, coil spring washer 607 and coil spring 608 are illustrated in FIG. 6 as well. Riser 603 is generally cylindrically shaped and extends from the adapter flange 604 to the base plate 602.

FIG. 6A is an enlarged portion 600A of FIG. 6. FIG. 6A illustrates the lever 601, the Hall Effect sensor 609, the reflective object sensor 610, the magnet 611, the magnet boss 612, the reflective surface 613, the reflective surface boss 614, the ball 615, and the ball spring adjuster 616.

FIG. 6B is a right side view 600B of the gas sensor apparatus of FIG. 5. Switches 618A-D are illustrated attached to the switch printed circuit board 501. Switch PCB connector PCB 502 and the switch PCB flexible circuit element 503 are illustrated in FIG. 6B as well. Third 617B and fourth 617D thermistors are illustrated along with their respective stalks 617A, 617C.

FIG. 10 is a front view 1000 of the sensor internal components. Ball 615 is illustrated in FIG. 10 as is switch actuator element adjuster screw boss 1001. FIG. 10A is front view 1000a of the gas sensor apparatus internal components with the riser cutaway illustrating the bellows 1003. Bellows lever coupling 1002 is illustrated in FIG. 10A in engagement with lever 601. Lever 601 is movable vertically depending on the pressure applied to the bellows and depending on the action of the bimetallic hinge. As shown in FIGS. 10 and 10A, gap 1004 is the distance between the lever 601 and the ball 615, in other words reference numeral 1004 is the lever displacement dimension.

FIG. 10B is an enlargement 100B of a portion of FIG. 10A illustrating the gap 1004 between the lever 601 and the spring loaded ball 615. As illustrated in FIGS. 10, 10A and 10B, vertically movable lever 601 is positioned by virtue of pressure greater than 60 psig and less than 82 psig.

The ideal gas law restated:

$$pV = nRT \therefore n = \frac{pV}{RT} \quad (1)$$

p=absolute pressure (pounds per square inch or psi)
V=volume (cubic meters)
T=temperature (Kelvin)
n=gas quantity in moles (mol)
R=gas constant=$1.2095 \times 10^{-3}$ It should be noted that, p, the pressure in (1) is the absolute pressure (reference to a vacuum) which differs by atmospheric or barometric pressure from the pressure indicated by a typical gauge in atmospheric conditions. This can be stated mathematically as:

$$p = p_{abs} = p_g + p_{atm} \quad (3)$$

p=$p_{abs}$=absolute pressure (psi)
pg=gauge pressure (psi)
$p_{atm}$=atmospheric pressure (psi)

With n the gas quantity in mol known, the mass quantity for a particular gas is derived from its molar weight:

$$m = nM_m \quad (4)$$

m=gas quantity in grams (g)
n=gas quantity in moles (mol)
$M_m$=molar mass of gas species (g/mol)

A sequence of measurements of gas mass $m_i = m_1, m_2, \ldots m_j$ can be derived using corresponding sequences of pressure $p_i$ and temperature $T_i$ measurements given only that the volume V, atmospheric pressure $p_{atm}$, and gauge pressure $p_g$ corresponding to each point in the sequence are known. A change in gas mass foretells a leak when a measurement $m_j$ is less than a measurement $m_k$ made sometime earlier (k<j). Conversely, the addition of gas is detected when $m_j$ is greater than $m_k$. In a non-leaking system, all of the $m_i$ will be substantially equal.

Figure 18:
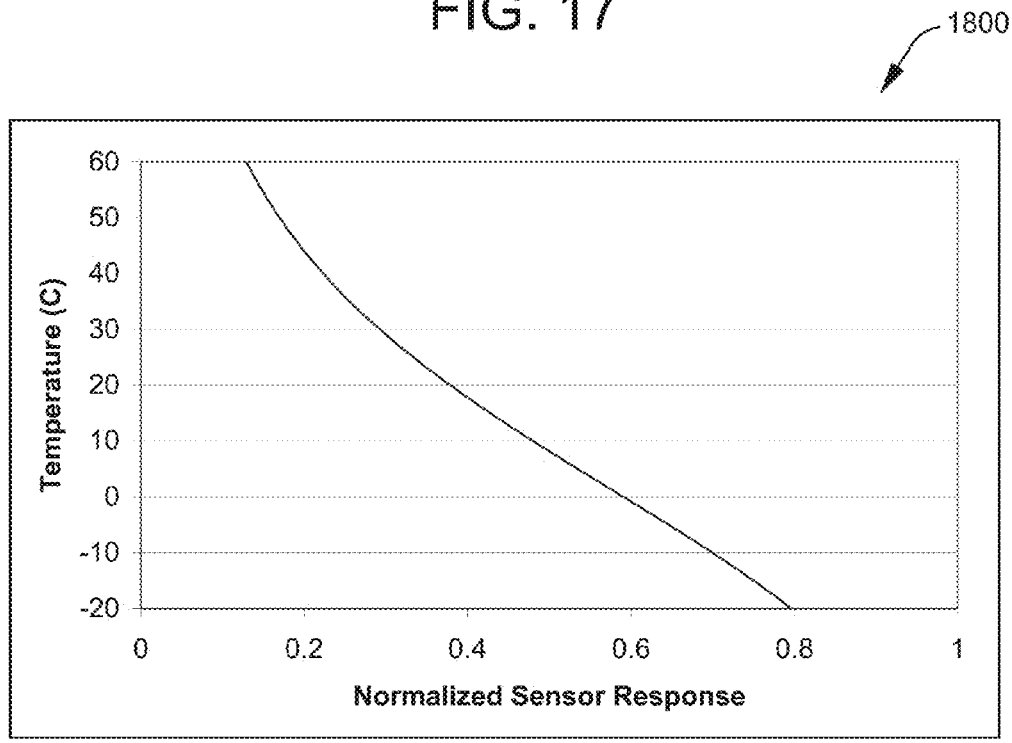
FIG. 18 is a graph of temperature of normalized temperature sensor response.

Acquiring temperature sequence $T_i$ begins by microcontroller 1301 using analog to digital converter 1303 applied to temperature interface 1307 accessing temperature probes 1308A through 1308D to acquire raw sensor measurements. Raw sensor measurements are then converted to accurate temperature readings through a calibration process such as that depicted in FIG. 18 wherein sensor response is converted to temperature in degrees centigrade for each sensor. Centigrade temperatures are converted to requisite absolute temperatures by addition of the offset 273.15 degrees. A point $T_i$ can then be recorded as a particular weighted average of the different sensor's derived absolute temperatures. In the preferred embodiment, the temperature sensors 1308A through 1308D correspond to thermistors 507B, 507D, 617B, and 617D.

Acquiring pressure sequence pi is somewhat more involved. It begins again with microcontroller 1301 using analog to digital converter 1303 applied to displacement interface 1309 accessing high resolution displacement transducer 1310 to acquire raw displacement sensor measurements. Unlike temperature measurements, there is no simple transformation of raw displacement measurements to absolute pressure, however. Firstly, a raw displacement sensor measurement is utilized by the MCU to compute calibrated lever displacement dimension according to calibration data such as that depicted in FIG. 16. In a preferred embodiment, the high resolution displacement transducer is the combination of a reflective object sensor 610 in combination with a reflective surface 613. In this case sensor response is calibrated using data such as that of curve 1601. In another embodiment, the high resolution displacement transducer is the combination of Hall Effect sensor 609 in combination with magnet 611. In this case sensor response is calibrated using data such as that of curve 1602.

Once calibrated lever displacement dimension is derived, initial gauge pressure estimate can be computed using secondary calibration data as depicted in FIG. 15. For example, if Hall Effect sensor response is measured to be 0.55 (1603), lever displacement dimension is determined to be 0.026 inch (1604). This lever location 0.026 inch can be transferred to the graph of FIG. 15 (1503) and used to determine an initial gas gauge pressure estimate of 82 psi (1604).

The intrinsic temperature compensation of the lever system comprising bi-metal hinge 708 must now be taken into account. In the absence of the bi-metal element, lever position would simply track temperature variations. For the fixed volume V, gas pressure increases proportional to increasing temperature (and vice versa). With only the resistance of coil spring 608, lever dimension 1004 would increase proportionately with the varying force exerted by bellows 1003. The bi-metal element is conceived to neutralize this temperature induced pressure variation. As temperature increases, the bi-metal exerts approximately equal magnitude equal force directed oppositely to the increased upward force of the bellows with the approximate result that the lever dimension remains constant. The converse occurs as temperature decreases. These mechanics alone allow the mechanism to operate as a low resolution density monitor wherein eventual changes in lever position represent approximate changes in gas mass (as opposed to pressure variations due to temperature), and, for fixed volume V, gas density. With the advent of the microcontroller in the present invention, it is possible to improve accuracy and flexibility of gas monitoring including the electronic measurement of pressure, temperature, gas content, and gas density as explained above.

Figure 17:
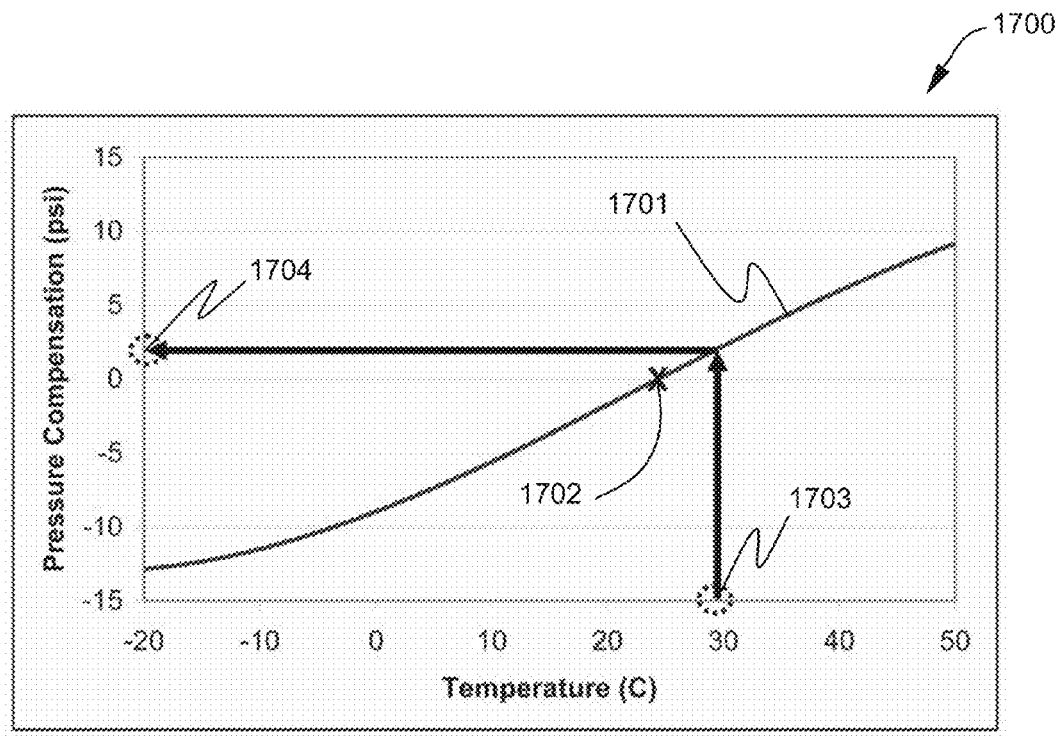
FIG. 17 is a graph of pressure compensation required as a function of temperature.

To complete the derivation of absolute gas pressure p from displacement and temperature sensor measurements, the initial gas gauge pressure estimate as above must itself be compensated for the temperature behavior introduced by the bi-metal element. The appropriate compensation is derived from the data in FIG. 17 using temperature Ti as above. For example, if Ti is 303K corresponding to a temperature of 29.85 C (1703), a temperature compensation of approximately 2 psi is indicated (1704). Therefore, in the current example, a calibrated gauge pressure is computed equal to 82 psi+2 psi equals 84 psi. A reasonable estimate of atmospheric pressure is used based on typical or measured data. An example of a typical value for atmospheric pressure is 14.7 psi. The measurement of absolute pressure $p_i$ is computed as the sum of the gas gauge pressure and the atmospheric pressure, 98.7 psi in the example.

To complete the example, given a typical tank volume V of 1 cubic meter, along with a molar mass for $SF_6$ gas of 146.055 g/mol, the gas mass $m_i$ is computed according to (1) and (4) to be 38.62 kg. The entire process is implemented by microcontroller 1301 in combination with the electronic elements of FIG. 13 and is represented in block diagram form in FIG. 14. All data described above is recorded in microcontroller memory including the raw sensor measurements through the final derived measurement sequences $T_i$, $p_i$, and $m_i$.

Figure 19:
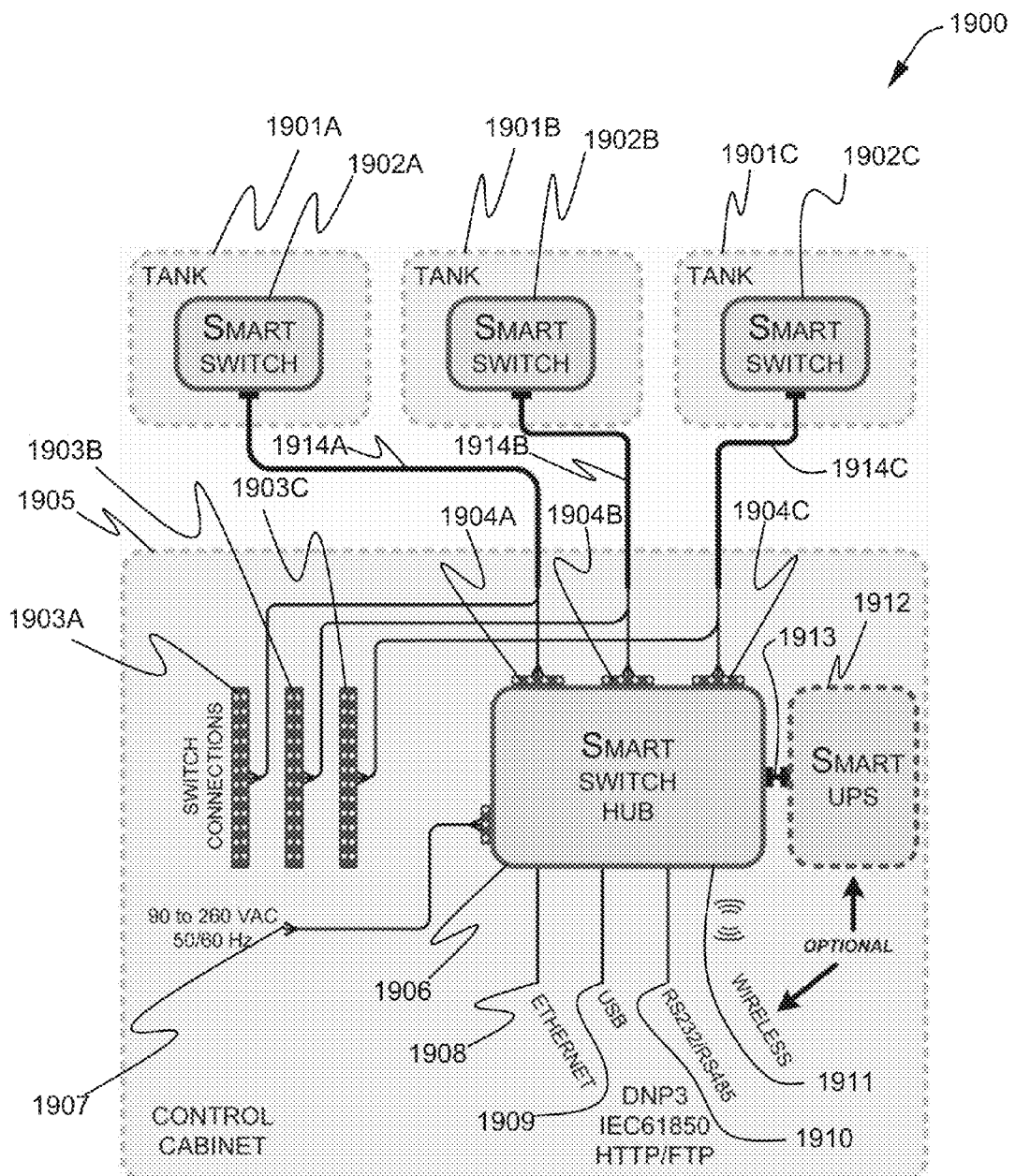
FIG. 19 is a block diagram of the gas sensor system in a 3-phase breaker application.
Figure 20:
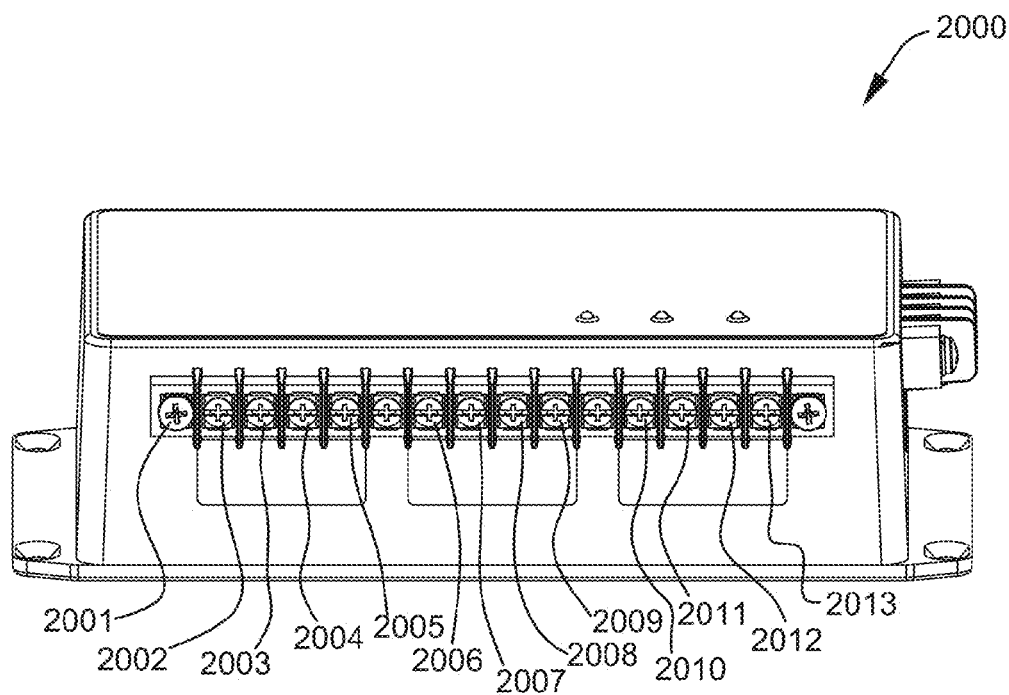
FIG. 20 is a side perspective view of a gas sensor hub module.
Figure 21:
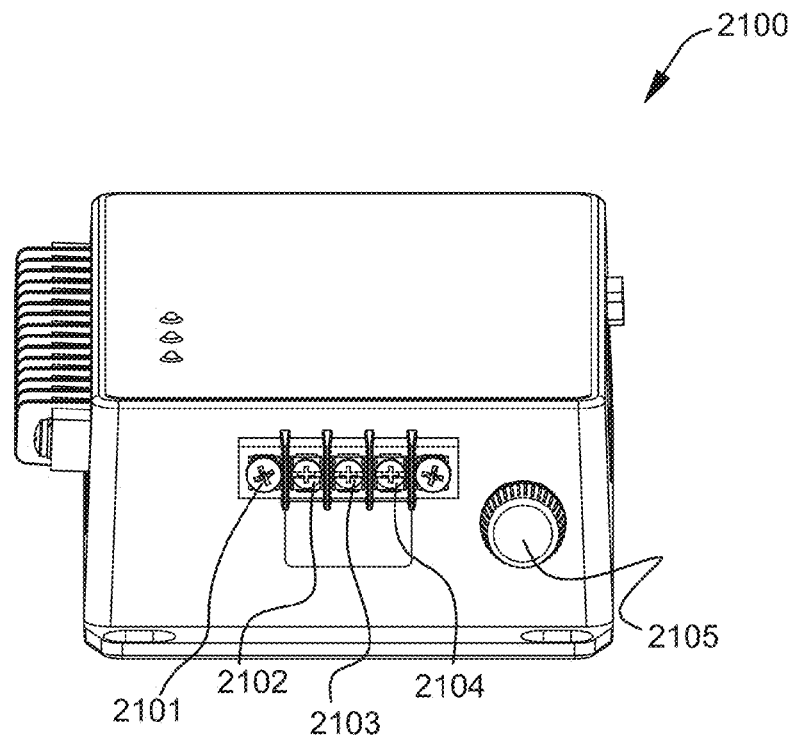
FIG. 21 is an end perspective view of a gas sensor hub module.
Figure 22:
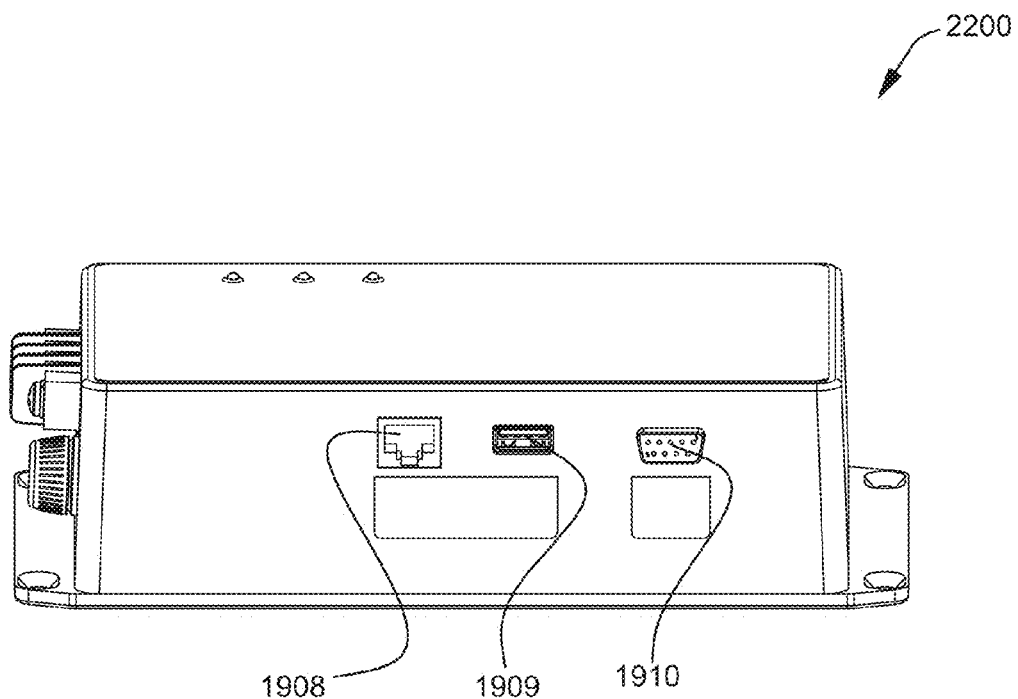
FIG. 22 is an opposite side perspective view of a gas sensor hub module.
Figure 23:
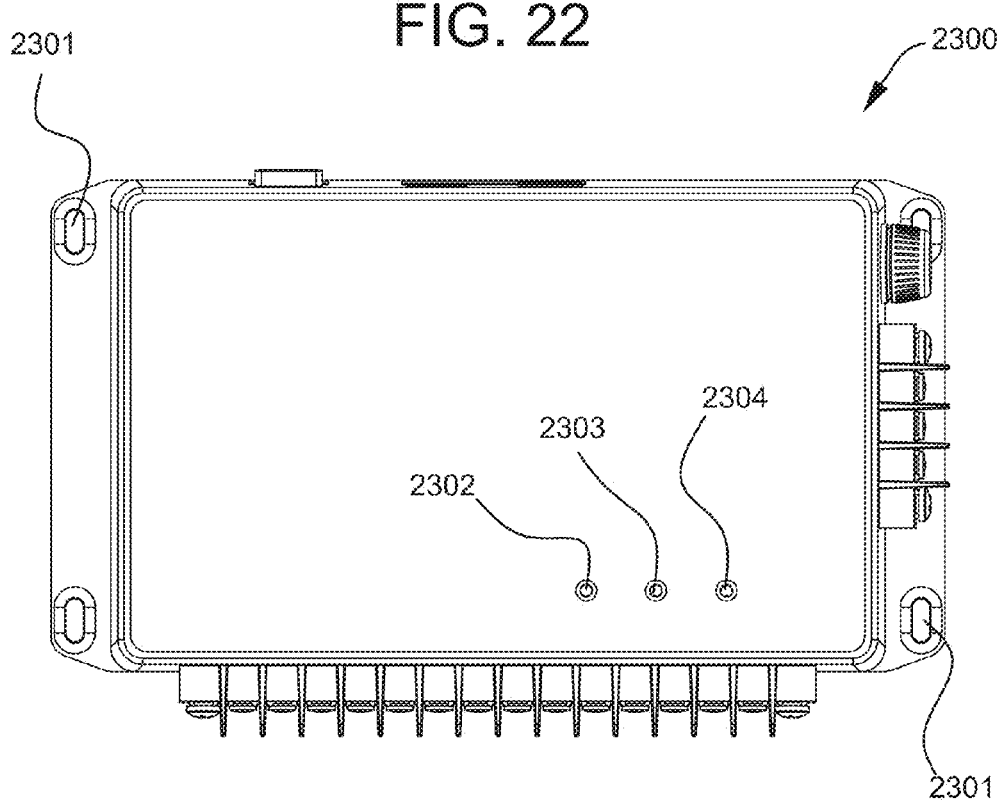
FIG. 23 is a top view of a gas sensor hub module.
Figure 28:
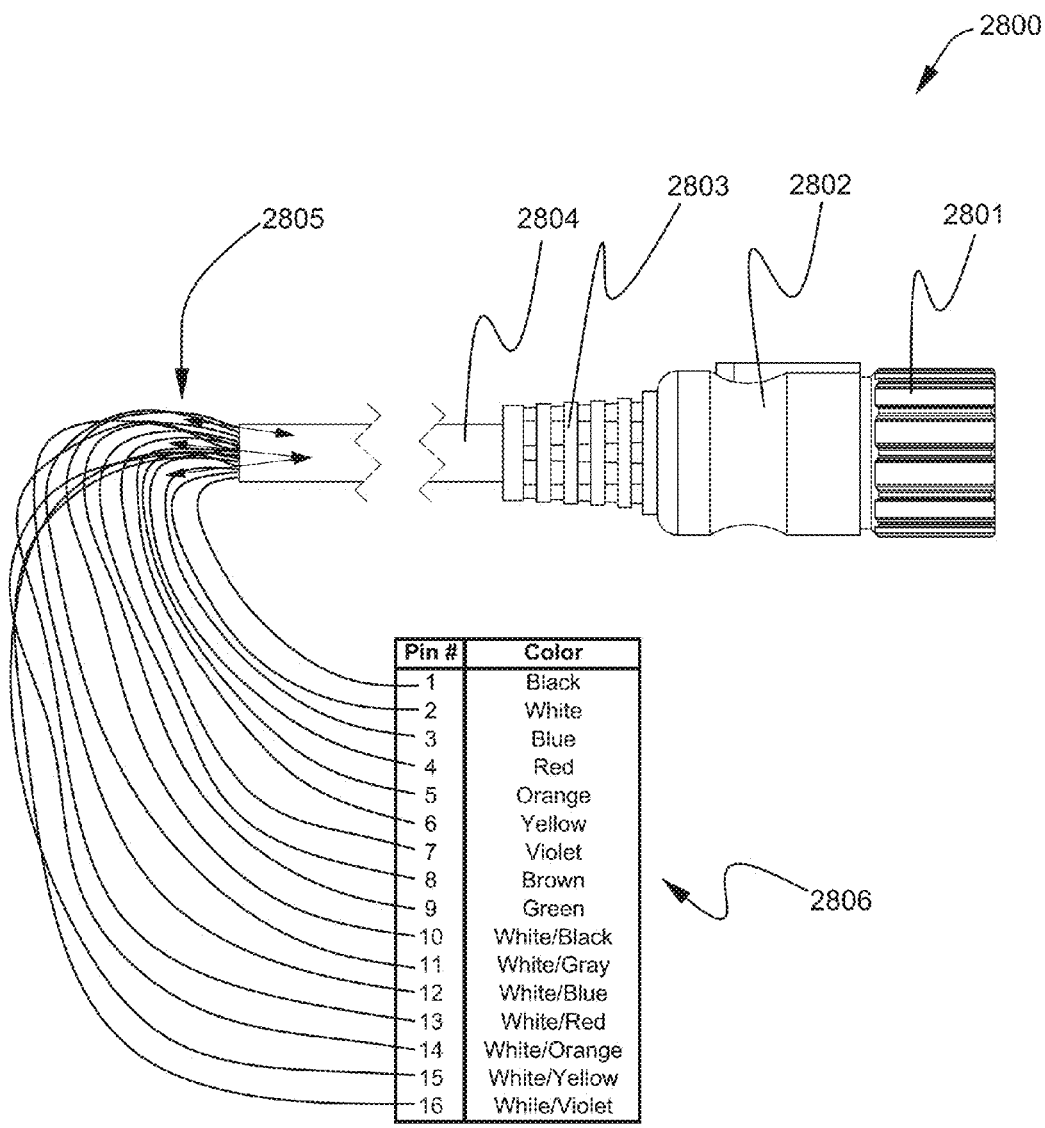
FIG. 28 is a multi-conductor cable for interconnecting a gas sensor with a gas sensor hub module.

In one embodiment of the invention, the gas sensor system utilizes a gas sensor apparatus mounted to the gas tank and connected via a multi-conductor cable (FIG. 28) to a gas sensor hub module (hub) mounted inside a breaker control cabinet. This embodiment is shown in schematic fashion in FIG. 19.

FIGS. 20, 21, 22, and 23 show various interfaces and mounting provisions of the hub. The hub is an important aspect of the instant invention. A single hub can interface multiple gas sensor apparatuses (three a least, one for each phase of a 3-phase electrical distribution system). The hub can also interface computers used by service personnel as well as the network management system of the operating company using physical and logical communications protocols specifically adapted and standardized by the industry for those purposes.

Figure 24:
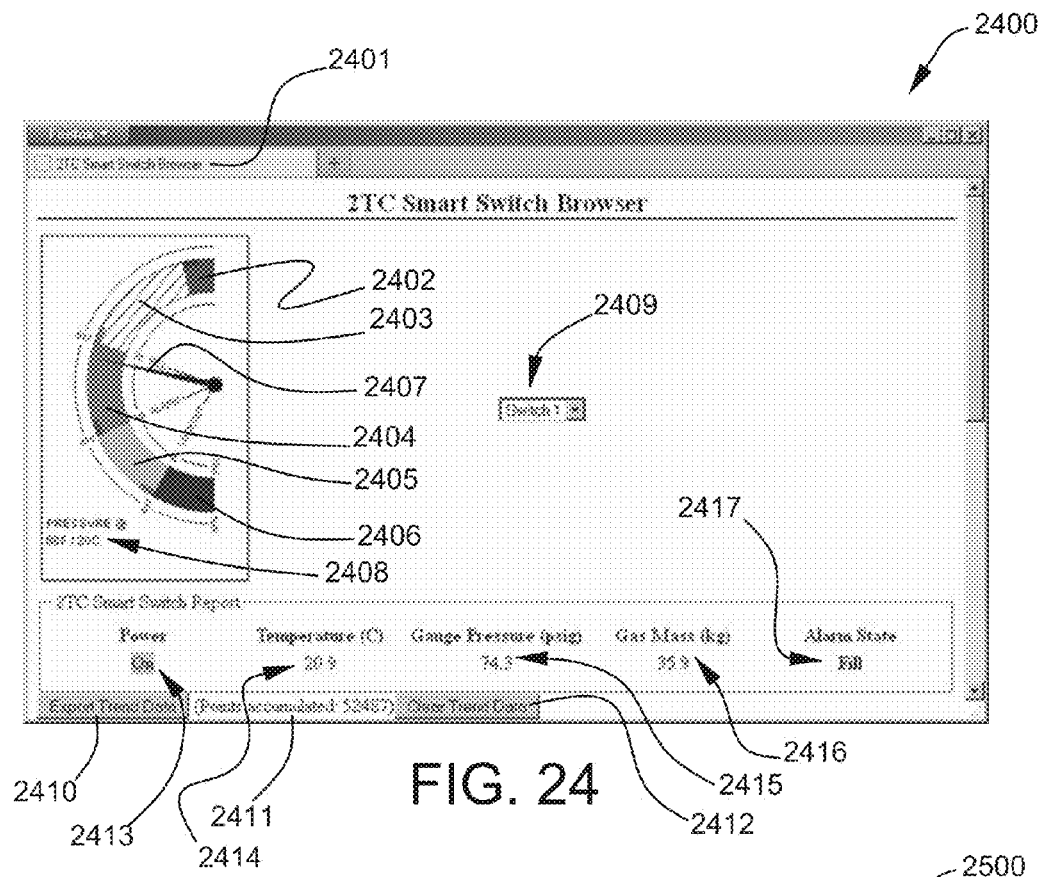
FIG. 24 is a graphical user interface gas sensor reporting screen.

FIG. 24 shows a graphical display of a human interface component where a human observer can easily visualize operating variables monitored and computed by the gas sensor system. These variables include power status, temperature, gauge pressure, gas mass, alarm status, and temperature compensated gas pressure.

Figure 25:
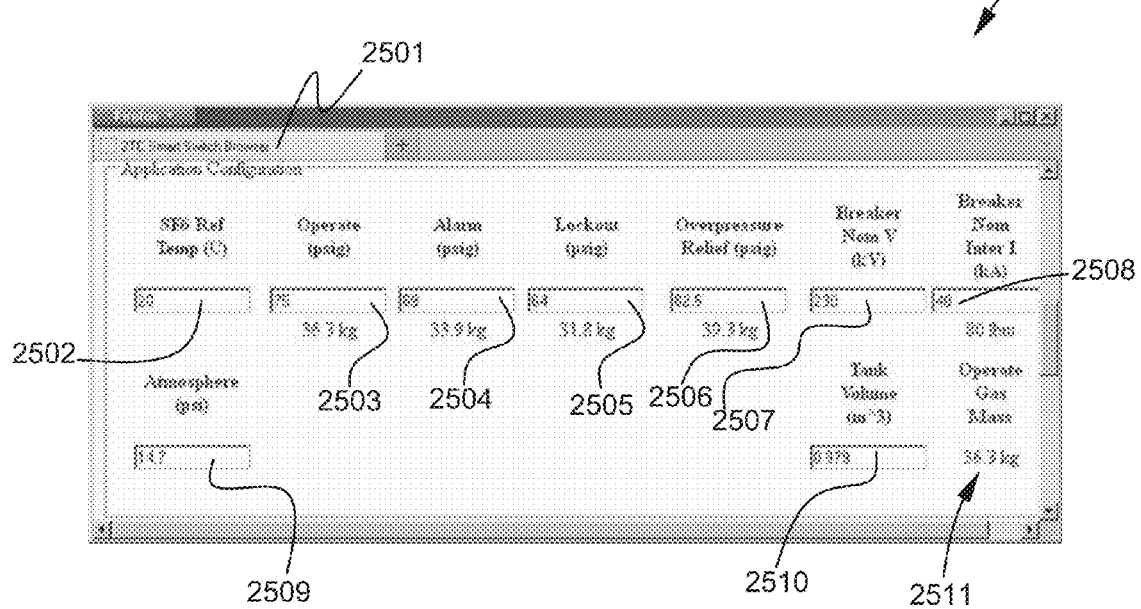
FIG. 25 is a graphical user interface gas sensor configuration screen.

FIG. 25 is another graphical display of a human interface component where a human operator can select various operating values that control the operating of the gas sensor system. These operating values include a reference temperature, pressure settings for operate, alarm, lockout, and over pressure thresholds, nominal breaker voltage and current, atmospheric pressure, and breaker gas tank volume. The value of gas mass corresponding to the operate pressure setting, the reference temperature setting, and the tank volume setting is computed and displayed.

As described above, the gas sensor system records measured and computed data in time. FIG. 26 shows a typical, tabular presentation of such data including temperature, pressure, gas mass, and alarm state for each instant in time (each row in the table).

Figure 27:
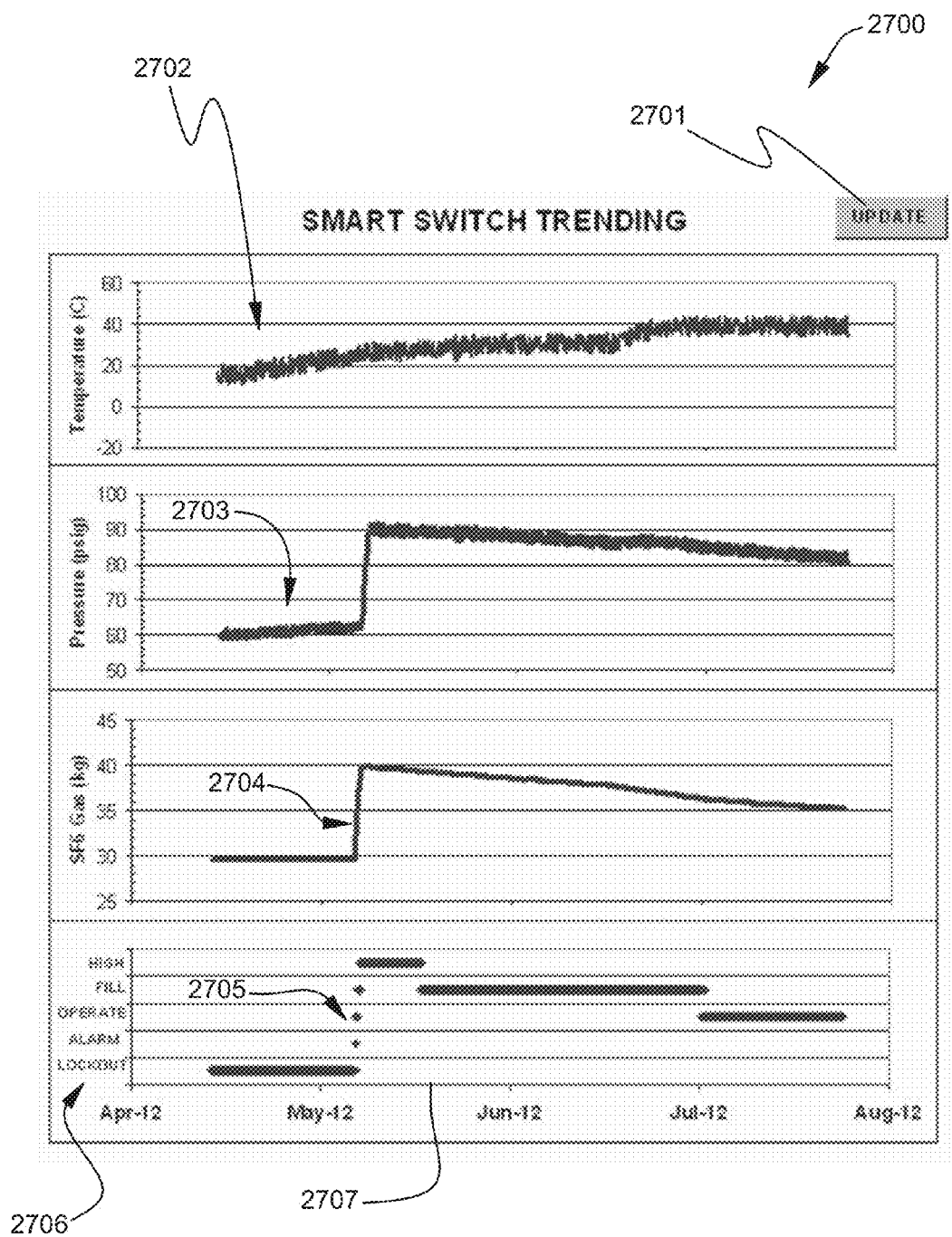
FIG. 27 is a graphical representation of gas sensor numerical data.

The recorded data can be view graphically as well. This is shown in FIG. 27.

The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, an all changes which come within the meaning and range of equivalency of the claims are therefore intended to be embraced therein.

REFERENCE NUMERALS

100 perspective view of sensor
101 cover
102 liquid tight pushbutton
103 cover retaining screw
104 housing
105 sensor connector
105A sensor connector contact pin
105B connector nut
106 manifold block
106A manifold block bolt hole
106B first gas port
107 display deadfront
107A deadfront gasket edge
200 perspective view of the sensor with cover and housing removed
202 pushbutton cable
203 pushbutton cable connector
204 processor PCB pushbutton connector
205 processor PCB
204 processor PCB pushbutton connector
205 processor PCB
300 perspective view of the sensor with pushbutton removed
301 display PCB
302 display PCB retaining screw
303 display PCB standoff
304 display digit
305 display PCB processor PCB connector
306 display PCB coil spring clearance hole
204 processor PCB pushbutton connector
205 processor PCB
400 perspective view of the sensor with display PCB removed
401 processor PCB retaining screw
402 processor PCB standoff
403 processor PCB coil spring clearance hole
404 processor PCB display PCB connector
405 processor PCB switch PCB connector
105 sensor connector
105A sensor connector contact pin
500 perspective view of the sensor with processor PCB removed
501 switch PCB
502 switch PCB connector PCB
503 switch PCB flexible circuit element
504 switch PCB retaining screw
505 switch PCB processor PCB connector
506 switch connections
507 thermistor connections
507A thermistor
507B thermistor stalk
508 reflective object sensor connection
509 switch PCB coil spring and switch adjustment clearance cutout
507A first thermistor stalk
507B first thermistor
507C third thermistor stalk
507D third thermistor
600 left side view of the sensor internal components
600A detail of lever and displacement mechanisms
600B right side view of the sensor internal components
600A detail of lever and displacement mechanisms
601 lever
602 base plate
603 riser
604 adapter flange
605 second gas port
606 coil spring nut
607 coil spring washer
608 coil spring
601 lever 609 Hall effect sensor
610 reflective object sensor
611 magnet
612 magnet boss
613 reflective surface
614 reflective surface boss
615 ball
616 ball spring adjuster
617A third thermistor stalk
617B third thermistor
617C fourth thermistor stalk
617D fourth thermistor
618A first switch
618B second switch
618C third switch
618D fourth switch
619 bimetal hinge base retaining plate
620 bimetal hinge base retaining plate nut
700 top view of the sensor lever and switch actuator elements
701 coil spring stud
702 switch actuator element adjuster screws
703 unused actuator element adjuster screw threaded hole
704 switch actuator elements
705 switch actuator elements flange screw
706 bimetal hinge lever retaining plate
707 bimetal hinge lever retaining plate nut
708 bimetal hinge
709A first switch PCB mounting boss
709B second switch PCB mounting boss
709C third switch PCB mounting boss
709D fourth switch PCB mounting boss
800 bottom view of switch PCB
800A perspective view of switch PCB from bottom
900A perspective view of sensor internal components from bottom
1000 front view of sensor internal components
1001 switch actuator element adjuster screw boss
1000A front view of sensor internal components with riser cutaway
1000B front view of lever displacement detail
1002 bellows lever coupling
1003 bellows
1004 lever displacement dimension
1004 lever displacement dimension
1100 top view of sensor internal components
1100A crosssection view from right side of sensor internal components
1101 gas port
1102 sensor module
1103 processor module
1104 stabilizer
1200 top view of sensor internal components
1200A crosssection view from front of sensor internal components
1300 hardware block diagram
1301 MCU (microcontroller unit)
1302 communication subsystem
1303 analog to digital converter subsystem
1304 digital to analog converter subsystem
1305 digital I/O interface subsystem
1306 safety limit detection subsystem
1307 temperature interface
1308A first temperature sensor
1308B second temperature sensor
1308C third temperature sensor
1308D fourth temperature sensor
1309 displacement transducer interface subsystem
1310 high resolution displacement transducer
1311 battery
1312 network management controller
1400 processing block diagram
1401 raw conversions from displacement and temperature subsystems
1402 signal to noise enhancement
1403 displacement to pressure calculation
1404 pressure calibration
1405 digital filtering subsystem
1406 signal processing parameter set
1407 pressure readings output to gas mass calculations and user interfaces
1500 lever position as a function of gas pressure at 25 C
1501 lever response from 0 psig to 60 psig, ball nose spring plunger operating
1502 lever response from 60 to 100 psig, coil spring and bimetal hinge only
1503 a particular lever position of 0.026"
1504 a pressure of 81 psig corresponds to position of 0.026"
1600 normalized sensor response as a function of lever position
1601 response of reflective object sensor
1602 response of Hall effect sensor
1603 a particular HES sensor response of 0.55
1604 a particular lever position of 0.026" corresponds to sensor response of 0.55
1700 graph of pressure compensation required as a function of temperature
1701 pressure compensation required as a function of temperature
1702 zero compensation required at reference temperature
1703 a particular temperature
1704 a particular pressure compensation corresponds to a particular temperature
1800 graph of temperature as a function of normalized temperature sensor response
1900 block diagram of the gas sensor system in a 3-phase breaker application
1901A first breaker tank
1901B second breaker tank
1901C third breaker tank
1902A first gas sensor on first breaker tank
1902B second gas sensor on second breaker tank
1902C third gas sensor on third breaker tank
1903A first switch contact terminal interface for first gas sensor
1903B second switch contact terminal strip interface for second gas sensor
1903C third switch contact terminal strip interface for third gas sensor
1904A first switch hub interface terminal strip for first gas sensor
1904B second switch hub interface terminal strip for second gas sensor
1904C third switch hub interface terminal strip for third gas sensor
1905 breaker control cabinet
1906 gas sensor hub module
1907 power input for gas sensor hub module
1908 Ethernet interface of sensor hub module
1909 USB interface of sensor hub module
1910 serial communications interface of sensor hub module
1911 wireless network interface of sensor hub module
1912 uninterruptible power module
1913 connection between sensor hub module and uninterruptible power module 1914A first cable interconnecting first gas sensor with first contact and hub terminal strips
1914B second cable interconnecting first gas sensor with second contact and hub terminal strips
1914C third cable interconnecting first gas sensor with third contact and hub terminal strips
2000 side perspective view of a gas sensor hub module
2001 terminal strip retaining screw
2002 first terminal of first hub interface terminal strip
2003 second terminal of first hub interface terminal strip
2004 third terminal of first hub interface terminal strip
2005 fourth terminal of first hub interface terminal strip
2006 first terminal of second hub interface terminal strip
2007 second terminal of second hub interface terminal strip
2008 third terminal of second hub interface terminal strip
2009 fourth terminal of second hub interface terminal strip
2010 first terminal of third hub interface terminal strip
2011 second terminal of third hub interface terminal strip
2012 third terminal of third hub interface terminal strip
2013 fourth terminal of third hub interface terminal strip
2100 end perspective view of a gas sensor hub module
2101 power input terminal strip retaining screw
2102 first terminal of power input terminal strip
2103 second terminal of power input terminal strip
2104 third terminal of power input terminal strip
2105 fuse of gas sensor hub module
2200 opposite side perspective view of a gas sensor hub module
2300 top view of a gas sensor hub module
2301 mounting flange of gas sensor hub module
2302 first annunciator of gas sensor hub module
2303 second annunciator of gas sensor hub module
2304 third annunciator of gas sensor hub module
2400 reporting screen of graphical user interface of gas sensor
2401 identifying tab of reporting page
2402 overpressure region of graphical pressure indicator
2403 operating pressure region of graphical pressure indicator
2404 below fill pressure region of graphical pressure indicator
2405 alarm pressure region of graphical pressure indicator
2406 operation lockout pressure region of graphical pressure indicator
2407 virtual needle pointer of graphical pressure indicator
2408 reference temperature for graphical pressure indicator
2409 selection, gas sensor
2410 export trend data virtual pushbutton
2411 indicator, number of entries accumulated in the data log
2412 clear trend data virtual pushbutton
2413 indicator, power status
2414 indicator, temperature
2415 indicator, gauge pressure value
2416 indicator, calculated gas mass content
2417 indicator, alarm state
2500 gas sensor configuration screen of graphical user interface
2501 identifying tab of configuration page
2502 selection, reference temperature
2503 selection, operate pressure threshold
2504 selection, alarm pressure threshold
2505 selection, lockout pressure threshold
2506 selection, over pressure relief threshold
2507 selection, nominal breaker voltage threshold
2508 selection, nominal breaker interrupting current threshold
2509 selection, atmospheric pressure
2510 selection, tank volume
2511 indicator, gas mass corresponding to operate pressure at reference temperature
2600 table of gas sensor numerical data from data log
2601 data column, time stamp
2602 data column, temperature
2603 data column, pressure
2604 data column, gas mass
2605 data column, alarm state
2700 graphical representation of gas sensor numerical data
2701 update graphical data virtual pushbutton
2702 graph, temperature versus time
2703 graph, pressure versus time
2704 graph, gas mass versus time
2705 graph, alarm state versus time
2706 y axis, particular alarm states
2707 x axis, time
2800 multi-conductor cable for interconnecting a gas sensor with a gas sensor hub module
2801 mass termination connector for gas sensor at breaker tank
2802 over molded connector retainer
2803 over molded cable strain relief
2804 multi-conductor cable jacket
2805 individual conductors with jacket stripped away
2806 individual conductor color coding for connection to contact and hub terminal strips within control cabinet

The invention claimed is:

1. A gas sensor apparatus, comprising:
a flange;
a bellows;
said bellows supported by said flange;
a port, said port communicating gas between a gas reservoir and said bellows urging said bellows in an expanding direction;
a base plate, said base plate supported by said flange;
a bellows coupling, said bellows coupling includes a pivot portion;
a movable lever;
said bellows residing between said flange and said bellows coupling;
said bellows coupling residing between said bellows and said lever, said pivot portion of said bellows coupling engaging said movable lever displacing said lever to a displacement in response to the temperature and pressure of said gas;
an adjustable bias mechanism, said bias mechanism engages said lever;
a bimetallic element, said bimetallic element affixed to said lever and to said base plate;
an electronic distance sensor, said electronic distance sensor includes a first element affixed to said lever and movable therewith, and said sensor includes a second element;
an electronic microcontroller;
said second element of said electronic distance sensor detecting said distance between said first element of said electronic distance sensor and said second element of said electronic distance sensor, said electronic distance sensor outputting a signal representative of said distance between said first and second elements to said microcontroller, said distance between said first element of said electronic distance sensor and said second element of said electronic distance sensor used in calculating said displacement in response to the temperature and pressure of said gas;

a temperature sensor, said temperature sensor outputting a signal representative of said temperature of said bimetallic element and said gas to said electronic microcontroller;

said microcontroller determining a temperature compensated pressure of said gas within said gas reservoir based on at least said displacement and said temperature; and, said microcontroller determining the gas density within said gas reservoir based on at least said temperature compensated pressure of said gas within said gas reservoir as communicated through said port.

2. An apparatus as claimed in claim 1, wherein said electronic distance sensor is a Hall Effect sensor, and, wherein said first element of said electronic sensor is a magnet and said second element of said electronic distance sensor measures the voltage due to presence and strength of the magnetic field of the magnet.

3. An apparatus as claimed in claim 1, wherein said electronic distance sensor is a reflective object sensor, and, wherein said first element of said electronic sensor is a reflective surface and said second element of said electronic distance sensor is a phototransistor in combination with an LED emitter, and said phototransistor measures the distance between the first and second elements.

4. A gas sensor apparatus as claimed in claim 1, further comprising:
a gas sensor hub module, said gas sensor hub module includes:
an enclosure with mounting flanges and holes;
a terminal strip to interface said microcontroller;
a terminal strip to interface electrical power;
an interface port;
an interconnecting cable assembly comprising a connector for said microcontroller;
a multi-conductor, jacketed cable; and,
connecting elements for said gas sensor hub tem1inal strip.

5. A gas sensor as claimed in claim 1, further comprising:
a snap action switch;
said snap action switch includes an actuator;
said actuator of said snap action switch engages said lever when said gas within said reservoir is at specified pressure.

6. A gas sensor as claimed in claim 1, wherein said microcontroller outputs a control signal when said gas within said reservoir is at a specified pressure.

7. A gas sensor as claimed in claim 5, wherein said snap action switch includes contacts and said actuator alternately makes or breaks said contacts, and, said microcontroller monitors said contacts of said snap action switch to determine whether contacts of said actuator are closed (made) or open (broken).

8. A process for operating a gas sensor, comprising the steps of:
measuring the temperature of a gas and a bimetallic element with a temperature sensor;
biasing a pivotable lever with respect to a base plate;
flexibly interconnecting said pivotable lever to said fixed base plate using a bimetallic element, said bimetallic element exerting a variable bias force upon said lever as a function of temperature;
communicating gas between a gas reservoir and bellows, said bellows includes a bellows lever coupling, and said bellows lever coupling includes a pivotable portion;
pivoting said pivotable lever about said pivotable portion of said bellows lever coupling of said bellows;
urging said bellows and said pivotable portion of said bellows lever coupling in response to gas pressure in a direction toward or away from said base plate;
measuring, using an electronic distance sensor, displacement of said pivotable lever with respect to said base plate as a function of gas pressure within said bellows and as a function of temperature of said bimetallic element;
outputting a signal representative of said displacement of said pivotable lever with respect to said base plate as a function of gas pressure within said bellows and as a function of temperature of said bimetallic element to a microcontroller;
outputting a signal representative of said temperature of said gas and said bimetallic element to said electronic microcontroller;
determining, using said microcontroller, a temperature compensated pressure of said gas within said gas reservoir; and,
determining, using said microcontroller, gas density within said gas reservoir.

9. A process for operating a gas sensor as claimed in claim 8 wherein said electronic distance sensor is a Hall Effect sensor.

10. A process for operating a gas sensor as claimed in claim 8 wherein said electronic distance sensor is a reflective object sensor.

11. A process for operating a gas sensor as claimed in claim 8 wherein said temperature sensor is a thermistor.

12. A process for operating a gas sensor as claimed in claim 8, wherein said step of measuring displacement of said pivotable lever with respect to said base plate as a fm1ction of gas pressure within said bellows and as a function of temperature of said bimetallic element is performed using a plurality of electronic distance sensors.

\* \* \* \* \*